(12) United States Patent
Amini et al.

(10) Patent No.: US 11,621,090 B2
(45) Date of Patent: Apr. 4, 2023

(54) PLATFORM FOR ASSESSING AND TREATING INDIVIDUALS BY SOURCING INFORMATION FROM GROUPS OF RESOURCES

(71) Applicant: TRAYT INC., Redwood City, CA (US)

(72) Inventors: Malekeh Amini, Hillsborough, CA (US); Carl B. Feinstein, Stanford, CA (US); Shuanhu Wang, Mountain View, CA (US); Hetao Huang, Los Altos, CA (US); Madeleine S. Vagadori, San Mateo, CA (US); Eliott H. Jones, Menlo Park, CA (US); Hitesh Kalra, Redwood City, CA (US); Eric Saltzman, Redwood City, CA (US)

(73) Assignee: TRAYT INC., Redwood City, CA (US)

( * ) Notice: Subject to any disclaimer, the term of this patent is extended or adjusted under 35 U.S.C. 154(b) by 480 days.

(21) Appl. No.: 16/361,125

(22) Filed: Mar. 21, 2019

(65) Prior Publication Data

US 2019/0221320 A1 Jul. 18, 2019

Related U.S. Application Data

(63) Continuation of application No. PCT/US2017/052726, filed on Sep. 21, 2017.
(Continued)

(51) Int. Cl.
*G16H 80/00* (2018.01)
*G16H 10/60* (2018.01)
(Continued)

(52) U.S. Cl.
CPC ............ *G16H 80/00* (2018.01); *G06Q 10/10* (2013.01); *G16H 10/60* (2018.01); *G16H 15/00* (2018.01); *G16H 20/00* (2018.01); *G16H 50/70* (2018.01)

(58) Field of Classification Search
CPC ........ G16H 80/00; G16H 20/00; G16H 15/00; G16H 50/70; G16H 10/60; G06Q 10/10
See application file for complete search history.

(56) References Cited

U.S. PATENT DOCUMENTS 9,280,746 B2    3/2016   Lindhiem
2007/0027636 A1*  2/2007  Rabinowitz ............ G16B 20/20
                                                          705/2
(Continued)

OTHER PUBLICATIONS

Office Action for Swiss Patent Application No. 00373/19, dated Dec. 22, 2020; 3 pages.
(Continued)

*Primary Examiner* — Robert A Sorey
*Assistant Examiner* — Kimberly A. Sass
(74) *Attorney, Agent, or Firm* — Perkins Coie LLP; Al Araiza; Kristen Schunter

(57) ABSTRACT

Disclosed embodiments include a server computer system that can create a patient profile identifying a group of individuals including a user of a client device and only one patient corresponding to an individual other than the user of the client device. The patient profile can include an assessment and a treatment for the patient based on the assessment. The server computer system can receive, from the client device over a computer network, data values selected by the user of the client device, where the data values are indicative of observations of the patient's activity. The server computer system can further update the patient profile based on the received data values such that the data values influence the treatment, and send, to the client device over the computer network, a message including guidance for the user of the client device to implement the treatment.

27 Claims, 15 Drawing Sheets

Related U.S. Application Data

(60) Provisional application No. 62/397,816, filed on Sep. 21, 2016.

(51) Int. Cl.
  *G06Q 10/10*  (2023.01)
  *G16H 20/00*  (2018.01)
  *G16H 15/00*  (2018.01)
  *G16H 50/70*  (2018.01)

(56) References Cited

U.S. PATENT DOCUMENTS

| | | | |
|---|---|---|---|
| 2008/0052120 A1* | 2/2008 | Iliff | G16H 80/00 |
| | | | 705/2 |
| 2008/0071581 A1 | 3/2008 | Luttrell | |
| 2009/0176257 A1* | 7/2009 | Bahn | A61P 25/18 |
| | | | 435/7.92 |
| 2012/0029935 A1 | 2/2012 | Iliff | |
| 2013/0085780 A1 | 4/2013 | Braunstein et al. | |
| 2014/0157171 A1 | 6/2014 | Brust et al. | |
| 2014/0279762 A1* | 9/2014 | Xaypanya | H04L 63/145 |
| | | | 706/12 |
| 2014/0310016 A1* | 10/2014 | Kenney | G16Z 99/00 |
| | | | 705/2 |
| 2016/0198996 A1* | 7/2016 | Dullen | A61B 5/02055 |
| | | | 600/595 |

OTHER PUBLICATIONS

International Search Report of PCT/2017/052726, dated Nov. 27, 2017, 11 pages.

* cited by examiner

FIG. 8M

Tracking Challenges
Daily Log for Emily - Today

Migraine

Freqency — Times

Duration — Minutes

Severity [⟷ Goal]   Yesterday 4
1    2    3    4    5
○    ○    ⦿    ○    ○
Description for the selected value in the slider Quickly Bored
Did Emily meet his goal today?

< Back    Treatment Adherence >

FIG. 8N

Treatment Adherence
Daily Log for Emily - Today

Treatment overview
Questions

All medication taken?     No | Yes
Regular diet followed?    No | Yes
All supplements taken?    No | Yes
Therapy visited?          No | Yes Interventions
Spoken to a doctor?       No | Yes < Back    Summary >

FIG. 8O

Summary
Daily Log for Emily - Today

General
Today

Tracking Challenges
Migraine
3 times   1 hour   Severity 3
[⟷ Goal]
Quickly bored
Goal not met Treatment Adherance
Not all medication taken
Reason why this is the case. Only answers that diverge from the default will be shown in this summary to keep it brief.

< Back    Done >

FIG. 8P

Cancel    Opt-out    Done
Daily lot for Emily - Today

Activities Tracked
You can opt-out here for specific data we're tracking.

General                              ⌃
⊘ Temporary Illness
⊘ Unusual stress at home
⊘ Stressfull day at school
⊘ Sleep issues Tracking Challenges                  ⌃
⊘ Migraine
⊘ Quickly Bored Treatment Adherance                  ⌃
⊘ All medication taken?

PLATFORM FOR ASSESSING AND TREATING INDIVIDUALS BY SOURCING INFORMATION FROM GROUPS OF RESOURCES

CROSS-REFERENCE TO RELATED APPLICATIONS

This application is a continuation of PCT/US2017/052726, filed Sep. 21, 2017, which claims priority to U.S. Provisional Application Ser. No. 62/397,816, filed Sep. 21, 2016. The aforementioned applications are incorporated herein by reference in their entirety.

TECHNICAL FIELD

The disclosed teachings relate generally to techniques for assessing and treating individuals. More particularly, the disclosed teachings relate to a comorbidity-based platform that can assess patients based on observations by groups of resources and provide personalized feedback to treat the patients.

BACKGROUND

Successful patient outcomes largely depend on accurate diagnosis and treatments. A healthcare professional will typically assess a patient's symptoms to recommend diagnostic tests for suspected diseases or conditions. These diagnostic tests may include detailed questionnaires, physical examinations, and laboratory tests. In some cases, a portion of a patient's specific genetic sequence can be tested for known genetic conditions. The healthcare professional will diagnose the patient with a specific known disease or condition and then prescribe known treatments.

FIG. 1 is a flowchart illustrating a method 100 for diagnosing and treating a neurodevelopmental disorder. In step 102, a patient completes a broad questionnaire that includes hundreds of questions about the patient's behavioral symptoms. Each answer requires a "never," "sometimes," or "always" response. In step 104, the answers are processed and compared against a list of broad, clinically significant categories including neurodevelopmental disorders. In step 106, the patient completes an extensive behavioral questionnaire targeted to neurodevelopmental disorders. Again, each answer requires a "never," "sometimes," or "always" response. In step 108, the answers are processed to diagnose the patient with a specific neurodevelopmental type disorder. In step 110, treatments are prescribed based on the diagnosis.

The method 100 is largely a trial and error process. That is, a misdiagnosis is not uncommon because healthcare professionals make an educated guess about a possible disease or condition based on a patient's symptoms and pursue diagnostic tests in accordance with that educated guess. The method 100 is performed iteratively until the most suitable diagnosis and treatments are identified. Moreover, the scope of the diagnosis is limited to known diseases or conditions. In other words, a healthcare professional would not suspect a disease or condition that is not clearly defined and, as such, could not recommend an effective treatment.

Even if a healthcare professional could diagnose a patient by using existing methods, treating the patient remains largely a trial and error process that involves applying treatments that are deemed suitable for the diagnosis. Unsurprisingly, some patients respond well to certain treatments while other patients fail to experience successful outcomes. These practices have existed largely unchanged simply because they have become entrenched in the medical profession, and remain in effect because of the lack of any effective and adoptable alternatives that can provide better outcomes.

SUMMARY

Figure 1:
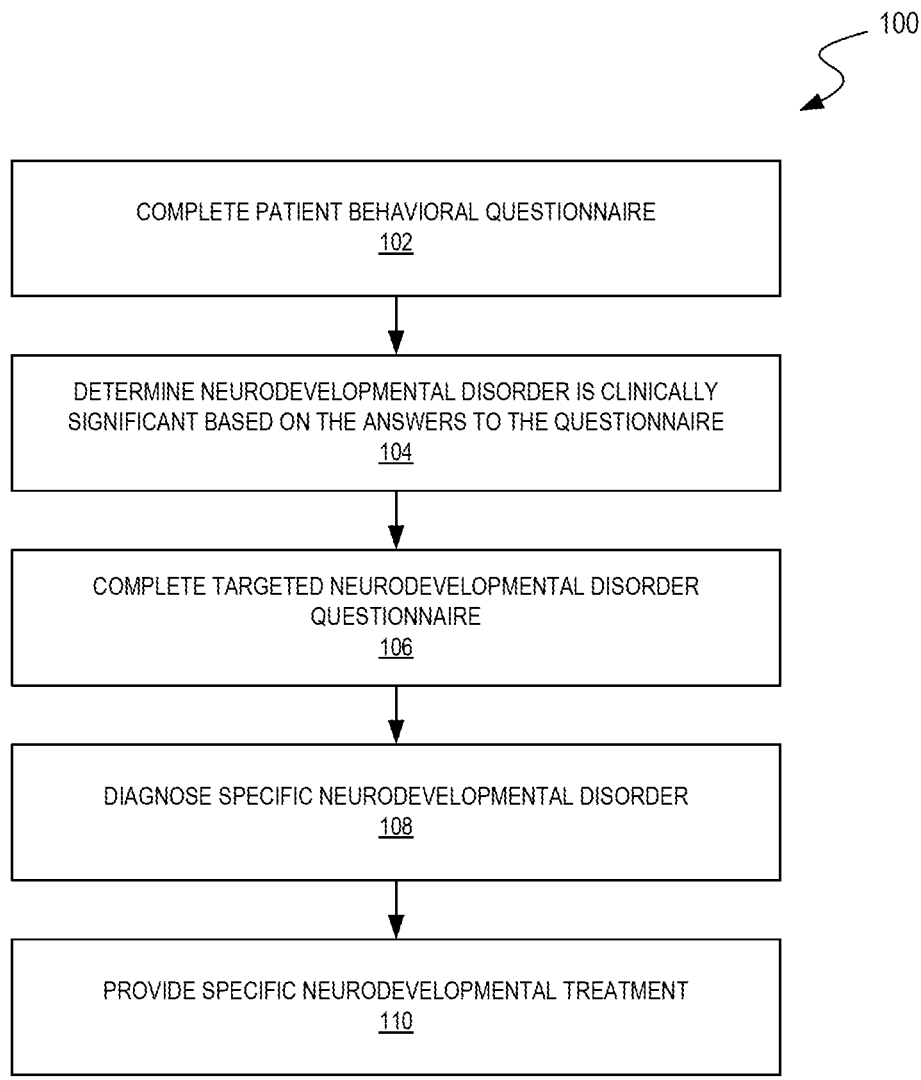
FIG. 1 is a flowchart illustrating a conventional method for assessing and treating individuals with a neurodevelopmental disorder.

Introduced herein is a technique including at least one server computer system and at least one method of the server computer system. The server computer system can create a patient profile identifying a group of individuals including a user of a client device and only one patient corresponding to an individual other than the user of the client device. The patient profile can include an assessment and a treatment for the patient based on the assessment. The server computer system can receive, from the client device over a computer network, data values selected by the user of the client device, where the data values are indicative of observations of the patient's activity. The server computer system can further update the patient profile based on the received data values such that the data values influence the treatment. Further, the server computer system can send, to the client device over the computer network, a message including guidance for the user of the client device to implement the treatment. In some embodiments, for example, the patient is a child and the user of the client device is the child's parent.

In some embodiments, the server computer system is further caused to, prior to sending the message to the client device, receive contextual information responsive to an occurrence of an event related to the patient's activity, and update the patient profile with the contextual information to influence the treatment and content of the message sent to the client device, where the message is sent responsive to updating the patient profile. In some embodiments, the contextual information indicates any of a change in the patient's activity, a location of the patient when the event occurred, an environmental measurement at the patient's location when the event occurred, or a point in time when the event occurred.

In some embodiments, the data values are responsive to a sequence of questions and includes a value identifying a symptom, a value indicating an intensity of the symptom, a value indicating a frequency of the symptom, and a value indicating a duration of the symptom. In some embodiments, the data values are adjusted by the patient's age and gender.

In some embodiments, the symptom is of a disorder or condition classified in the Diagnostic and Statistical Manual of Mental Disorders (DSM). In some embodiments, the symptom is of a disorder or condition that is not classified in the DSM.

In some embodiments, to update the patient profile includes causing the server computer system to generate the assessment based on the adjusted data values. In some embodiments, to update the patient profile includes causing the server computer system to generate the treatment based on the assessment, and select a measurable goal from multiple measurable goals for treating the patient such that the message sent to the client device includes the selected goal as a suggestion for treating the patient.

In some embodiments, the selected goal includes content suggesting a measurable action for the user to take in achieving the selected goal. In some embodiments, each of the selected goal and the action is measurable by intensity, frequency, and duration.

In some embodiments, the server computer system is further caused to track a progress of the selected goal and make suggestions to the user of the client device for additional actions depending on a level of the progress, where the additional actions are identified based on symptoms impacted by the selected goal. The server computer system is further caused to send, to the client device over the computer network, another message including guidance for the user of the client device to implement the additional actions, and update the patient profile with the selected goal and the tracked progress.

In some embodiments, the data values include a goal defined by the user for treating the patient such that the treatment is influenced by the user-defined goal.

In some embodiments, the data values include at least one value selected from a defined range of values consisting of 1, 2, 3, 4, or 5.

In some embodiments, the group includes users of respective client devices that each contribute to updating the patient profile and each receive a message including guidance for the users of respective client devices to implement the treatment.

In some embodiments, the server computer system is further caused to enable the group to exchange information of the patient profile with another group of another patient profile.

In some embodiments, the server computer system is further caused to administer a network portal to enable access to the patient profiles including outcomes of the treatments implemented by users of the groups.

In some embodiments, the server computer system is further caused to administer a network portal to enable viewing, analyzing, and managing the assessment and treatments of the patients.

In some embodiments, the server computer system is further caused to log incidents related to the patient's activity as the incidents occur, where each logged incident includes a time and context related to the occurrence of the incident.

In some embodiments, the server computer system is further operable to, prior to sending the message to the user of the client device receive, from one or more computer devices over the computer network, actively and passively collected data including any of: values each related to a disease or condition associated with the patient and including a value unrelated to a mental disorder, genomic information related to the disease or condition associated with the patient, or risk factors associated with the patient. The server computer system can then update the patient profile with the actively and passively collected data to influence the treatment and content of the message sent to the user of the client device.

In some embodiments, the server computer system is further caused to receive periodic data from the client device over the computer network. The periodic data being indicative of periodic inputs at the client device by the user. The server computer system can then send feedback data over the computer network to the client device, the feedback data being responsive to the periodic data such that the server computer system tracks changes in subsequently received periodic data relative to the feedback data.

In some embodiments, the patient profile of the patient is a first patient profile of a first patient that belongs to a first group of individuals. The server computer system is further caused to build patient profiles for a respective patients including the first patient profile of the first patient, generate comorbidity profiles based on the patient profiles, where each comorbidity profile is indicative of a simultaneous presence of a neurodevelopmental type disorder and at least one additional disease or condition in a patient. The server computer system is further caused to classify a second patient profile as belonging to one of the comorbidity profiles such that the second patient is associated with a neurodevelopmental type disorder and at least one additional disease or condition of the one of the comorbidity profiles, and send information related to the neurodevelopmental type disorder and the at least one additional disease or condition of the second patient over the computer network to a user of a client device in a second group including the second patient.

In some embodiments, the server computer system is further caused to classify each patient profile as belonging to one comorbidity profiles, where each comorbidity profile is indicative of a simultaneous presence of a neurodevelopmental type disorder and at least one additional disease or condition in a patient. The server computer system is further caused to send information related to the neurodevelopmental type disorder and the at least one additional disease or condition of the patient over the computer network to at least one client device of each group.

Embodiments also include a method performed by a server computer system including the steps described above.

Embodiments also include a non-transitory computer-readable storage memory storing instructions that, when executed by a server computer system, cause actions includes creating patient profiles each identifying a group of individuals including a user of a client device and only one patient corresponding to an individual other than the user of the client device, where each patient profile can include an assessment and a treatment for the respective patient based on the assessment. The actions also include receiving, from client devices over a computer network, data values selected by the users of the client devices, where the data values are indicative of observations of respective patients' activity. The actions also include updating each patient profile based on the received data values such that the data values influence the treatment for each patient, and sending, over the computer network to at least one client device of each group, a message including guidance to implement the treatment.

Embodiments also include a server computer system that can receive user-selected data values over a computer network from a client device in response to preset questions. Each user-selected value can be selected by a user of the client device from a predetermined range of values indicative of a severity of a behavioral symptom of a mental disorder of a patient. The server computer system can receive healthcare-generated values related to a disease or condition over the computer network from the client device or a remote server computer system, where at least some of the healthcare-generated values are unrelated to the mental disorder of the patient. The server computer system can build a patient profile based on the user-selected data values.

In some embodiments, the server computer system can receive periodic data from the client device over the computer network, where the periodic data is indicative of periodic inputs at the client device by the user, and send feedback data over the computer network to the client device, where the feedback data is responsive to the periodic data such that a service administered by the server computer system tracks changes in subsequently received periodic data based on the feedback data.

In some embodiments, the server computer system can build multiple patient profiles for multiple patients, and generate comorbidity profiles based on the patient profiles. Each comorbidity profile is indicative of a simultaneous presence of a neurodevelopmental type disorder and at least one additional disease or condition in a patient. The server computer system can classify a subsequent patient profile as belonging to a comorbidity profiles such that the subsequent patient is associated with a neurodevelopmental type disorder and additional diseases or conditions of the comorbidity profiles. The server computer can then send information related to the neurodevelopmental type disorder and the additional diseases or conditions of the subsequent patient over the computer network to a device associated with the subsequent patient.

In some embodiments, the server computer system can adjust the user-selected data values with respect to an age value and gender value of the patient.

In some embodiments, the server computer system can receive, over the computer network from a remote computer system, genomic information of the patient relating to target and non-target diseases or conditions associated with the patient. As such, the patient profile is built based on the genomic information in addition to the user-selected data values and healthcare-generated values.

In some embodiments, the server computer system can receive, from a computing device over the computer network, risk factor values associated with the patient, where the risk factor values were actively or passively collected by the computing device. As such, the patient profile can be built based on the risk factor values, the genomic information, the user-selected data values, and the healthcare-generated values.

In some embodiments, the server computer system can classify the patient profile as belonging to one of multiple comorbidity profiles, where each comorbidity profile is indicative of a simultaneous presence of a neurodevelopmental type disorder and at least one additional disease or condition in the patient. The server computer can then send information related to the neurodevelopmental type disorder and additional diseases or conditions of the patient over the computer network to the client device. In some embodiments, the neurodevelopmental type disorder can be autism.

In some embodiments, a behavioral symptom is associated with a disorder or condition classified in the DSM. In some embodiments, the behavioral symptom is related to a sleeping behavior, a repetitive behavior, or a hyperactive behavior.

In some embodiments, a healthcare-generated value is associated with a disease or condition not classified in the DSM. In some embodiments, the disease or condition not classified in the DSM is a gastrointestinal disease, a seizure, or a thyroid disease. The DSM and non-DSM comorbidities can range across many conditions and/or symptoms, which are not limited to a gastrointestinal disease, a seizure, or a thyroid disease. Many other conditions can be involved such as diabetes, hypertension, sleep disorder, strep throat, childhood deafness, etc.

In some embodiments, each of the user-selected values is selected from the predetermined range of finite values consisting of 1, 2, 3, 4, or 5.

In some embodiments, each of the user-selected values is selected from the predetermined range spanning continuously from 1 through 5.

This Summary is provided to introduce a selection of concepts in a simplified form that are further explained in the Detailed Description. This Summary is not intended to identify key features or essential features of the embodied subject matter, nor is it intended to be used to limit the scope of the embodied subject matter.

DETAILED DESCRIPTION

The embodiments set forth below represent the necessary information to enable those skilled in the art to practice the embodiments, and illustrate the best mode of practicing the embodiments. Upon reading the following description in light of the accompanying figures, those skilled in the art will understand the concepts of the disclosure and will recognize applications of these concepts that are not particularly addressed here. It should be understood that these concepts and applications fall within the scope of the disclosure and the accompanying claims.

The purpose of terminology used herein is only for describing embodiments and is not intended to limit the scope of the disclosure. Where context permits, words using the singular or plural form may also include the plural or singular form, respectively.

As used herein, unless specifically stated otherwise, terms such as "processing," "computing," "calculating," "determining," "displaying," "generating," or the like, refer to actions and processes of a computer or similar electronic computing device that manipulates and transforms data represented as physical (electronic) quantities within the computer's memory or registers into other data similarly represented as physical quantities within the computer's memory, registers, or other such storage medium, transmission, or display devices.

As used herein, terms such as "connected," "coupled," or the like, refer to any connection or coupling, either direct or indirect, between two or more elements. The coupling or connection between the elements can be physical, logical, or a combination thereof.

The disclosed technique includes a platform that can collect data related to patients to assess and treat those patients. A "patient" refers to an individual that is subject to an assessment or treatment. The platform can be implemented in a system that has users that are not subject to an assessment or treatment. For example, other users can monitor and track the activity of the patients and provide input about the patients to the platform, which can use that input to diagnose the patients. In the context of the platform, the other users have roles such as caregiver or doctor. The roles reflect different associations between a patient and the other users.

A group of resources that includes at least one patient is referred to as a "community." For example, a community of resources can include a patient and the patient's parent. The resources of a community can each have direct contact with the patient and the platform that used to assess and treat the patient. In some instances, the resources of a community can monitor the activity of its patient and record observations of the patient's activity to the platform. The data used to diagnose the patient could also be obtained directly from the patient, rather than indirectly from the patient's associated users in the same community. Moreover, other data used to diagnose the patient could also be obtained from devices such as fitness trackers, cameras, or other electronic devices that can actively or passively monitor activity of the patient.

The obtained data can be used individually or collectively to diagnose the patient. In this way, data can be collected from diverse sources and include data that has been actively input by non-patients about the patient, data actively input by the patient about the patient, and data about the patient passively obtained from computing devices. The platform can provide treatment feedback to the community based on the patient's diagnosis. As such, the non-patient members of the community can participate in an assessment and treatment of the patient, as wells as the patient and other passive devices, or combinations thereof. For example, the platform can set a goal for a community, and instruct the community members to act in accordance with that goal in an effort to treat the patient. This creates a positive feedback cycle to monitor and track the user, and adapt an assessment or treatment in light of changing activities that reflect changing circumstances or opportunities to improve the effectiveness of the platform.

In some embodiments, a comorbidity-based healthcare platform can collect a patient's diagnostic data, genetic data, symptom information, medication and supplement information, therapy information, diet information, demographic data, and the like. The platform can also track behavioral and treatment information of the patient on a regular basis (e.g., daily, weekly), as entered by different caregivers, including a parent, doctor, therapist, and teacher. This rich set of data, combined with external data such as from electronic medical records (EMRs), is used to build a profile for the patient, which can be used to assess and treat the patient. Upon assessing or diagnosing the patient, the platform can implement a treatment by formulating a plan and distributing instructions to resources of the patient's community.

Unlike conventional systems that involve trial and error and are prone to misdiagnosis and inadequate treatments, the disclosed platform can identify effective treatments by confirming or discovering comorbidities based on the patient's profile. A comorbidity is the simultaneous presence of two chronic diseases or conditions in a patient. For example, 22q11.2 gene deletion syndrome ("22q11.2DS") is a comorbid disease because it leads to a higher risk of schizophrenia and increases the risk of childhood anxiety. In this example, the 22q11.2DS can be diagnosed with a genetic test, and the anxiety can be tracked as a symptom (e.g., on a scale of 1-5).

The platform can thus confirm the comorbidity based on the collected dataset and recommend effective treatments in light of the patient's profile.

To discover comorbidities and classify a patient as having a comorbidity, the platform generates multiple comorbidity profiles from numerous patient profiles. Each comorbidity profile can indicate the simultaneous presence of, for example, a neurodevelopmental type disorder and additional diseases or conditions in a patient. The disclosed platform can perform comorbidity discovery analysis at a large scale rather than studying patients for a single study. Moreover, the platform can include services to track a patient's progress, which can be used in machine learning to improve classification and reclassification of patient profiles as being associated with specific comorbidity profiles.

In some embodiments, a comorbidity of a patient could be assessed according to dimensions including intensity, frequency, and duration, which can all be normalized by an individual's gender and age. The intensity can be a value defined on a scale of 1 to 5, where 5 indicates the highest intensity level. The frequency can be defined by how often a symptom of a comorbidity occurs at a certain intensity level. The duration can be defined by the duration of a symptom at a certain intensity level. Lastly, the comorbidity can be adjusted by the gender and/or age of the patient.

In some embodiments, the symptoms are observed by one or more members of a community that includes the patient. The patient may have a user profile that includes demographic information such as gender and age. The members of the patient's community can input values for the intensity, frequency, and duration of symptoms observed by the resources to a service provider. The platform can analyze the obtained data indicating the observations of the patient's activities to formulate an assessment and treatment plan for the patient. This information can be fed back to the community members, which can then input data indicative of observations of the patient's ongoing activities, which can be used to monitor and track the success or failure of the treatment.

The initial information in a patient's profile can be used to assess a user and formulate a treatment plan. Ongoing information sourced from various users or devices can then be used to monitor and track the patients progress. The platform can set a goal that involves the community including the patient. The platform can then provide instructions to the community of users to revise the treatment plan. As a result, the platform can assess a user, formulate a treatment, and optimize the treatment plan.

The assessment process can include an evaluation of a combination of a number of comorbidities used to assess a user. Specifically, the process for assessing the user can be distributed between a community and the backend of the system. For example, the community members can input severity values based on observations of the user's activities, and input data indicative of those values to the system via a network portal or software application. In some embodiments, the community members input dimensions of symptoms (e.g., intensity, frequency, and duration), and the backend of the system determines the severity of discovered comorbidities.

In some embodiments, a comorbidities assessment can involve answering a number of questions posed to users about a patient's observed behavior. The questions may be posed in different formats. For example, the platform may present alternatively or mutually selectable options about symptoms related to comorbidities of a patient.

An example of an assessment is described below but can vary according to different embodiments. In some embodiments, the platform can administer the assessment via a portal that prompts a user to input responses that cover a number of metrics posed in a particular order to optimize the assessment. The following description includes a number of metrics that can be used to assess an individual patient.

A metric for social communication or interaction could be given a value on a scale of 1 to 5. A value of 1 could indicate a "mild" level, which indicates that an individual presents immature conversation, communication, and language skills. The individual may occasionally have difficulty perceiving social cues and assessing social risk. The individual could be gullible but able to form healthy relationships with others outside of an immediate family or caregivers.

A value of 2 could indicate a "moderate" level, which indicates that the individual shows differences from peers in social and communicative behavior. The individual's communication, conversation, and language skills are more concrete or immature than expected for his or her age. The individual also has difficulty regulating emotion and assessing social risk. The individual may appear to have decreased interest in social interactions. Further, the individual is at risk for being manipulated by others due to a limited understanding of social situations.

A value of 3 could indicate a "significant" level, which indicates that the individual shows significant differences from peers in social and communicative development. The individual may routinely misinterpret social cues and require assistance to make social judgments and decisions. The individual's relationships are affected by communicative limitations, and the individual has difficulty initiating social interactions.

A value of 4 could indicate a "severe" level, which indicates that the individual has speech and spoken language skills limited to single words and phrases focused on present events due to limited a vocabulary and grammar understanding. The individual's speech is used mainly for social communication, and the individual understands simple speech and gestures. The individual may experience limited initiation of social interaction, and reduced or abnormal responses to social overtures.

Lastly, a value of 5 could indicate a "profound" level, which indicates that the individual has a very limited understanding of speech and gesture. The individual's expression of desire and emotion is done mainly through nonverbal communication. Relationships are limited to well-known individuals in which the individual responds to gestural and emotional cues. The individual could also have extremely limited initiation of social interaction and respond only to the most direct social approaches.

A metric for repetitive behavior or intolerance of routine changes could be given a value on a scale of 1 to 5. A value of 1 could indicate a "mild" level, which indicates that the individual shows inflexibility of behavior and resistance to change that occasionally interferes with functioning. The individual mostly or usually overcomes resistance to change and shifting attention. The individual may also experience repetitive behavior that occasionally interferes with functioning in some spheres.

A value of 2 could indicate a "moderate" level, which indicates that the individual shows inflexibility of behavior and resistance to change that impacts and sometimes interferes with functioning. The individual can often overcome resistance to change and shifting attention. The individual may also show repetitive behavior that sometimes interferes with functioning in some spheres.

A value of 3 could indicate a "significant" level, which indicates that the individual shows inflexibility of behavior and resistance to change that impacts and often interferes with functioning. The individual can sometimes overcome resistance to change and shifting attention. The individual also shows repetitive behavior that often interferes with functioning in some spheres.

A value of 4 could indicate a "severe" level, which indicates that the individual shows inflexibility of behavior and resistance to change that interferes with functioning. The individual may have significant difficulty coping with change and struggles to change or shift focus. The repetitive behavior may interfere with functioning in most spheres.

A value of 5 could indicate a "profound" level, which indicates that the individual shows extreme inflexibility of behavior and resistance to change. The individual may have profound difficulty coping with change and changing focus. The repetitive behaviors may markedly interfere with functioning in all spheres.

A metric for verbal communication could be given a value on a scale of 1 to 5. Examples of factors that contribute to this metric may include speaking rate, speaking fluency (e.g., pauses, silences, "uh" utterances), vocal confidence (e.g., neither too tense/nervous nor overly-confident sounding), articulation (e.g., clarity of pronunciation and linguistic expression), vocal variety (e.g., neither overly monotone nor dramatic voice), volume (e.g., neither too loud nor too soft), posture (e.g., neither too closed/formal nor too open/informal), lean toward partner (e.g., neither too forward nor too far back), facial expressiveness (e.g., neither blank nor exaggerated), nodding of head in response to partner statements, use of gestures to emphasize what is being said, use of humor and/or stories, smiling and/or laughing, use of eye contact, asking of questions, involvement of a partner as a topic of conversation, personal opinion expression, and/or maintenance of topics and follow-up comments.

A value of 1 could indicate a "mild" level, which indicates that the individual shows only a slight, rare, awkward, or disruptive communication, but otherwise has the use of communicative skills generally good. A value of 2 could indicate a "moderate" level, which indicates that the individual's use of communicative skills is sufficient but neither very noticeable nor excellent. A value of 3 could indicate a "significant" level, which indicates that the individual is often awkward or disruptive and occasionally has adequate use of communicative skills. A value of 4 could indicate a "severe" level, which indicates that the individual's use of communicative skills was usually noticeable in its absence, excess, or disruptiveness. A value of 5 could indicate a "profound" level, which indicates that the individual uses very little, if any, verbal communication. The individual's use of communicative skills is awkward, disruptive, or results in a negative impression of communicative skills.

An metric for obsessive compulsive behavior could be given a value on a scale of 1 to 5. A value of 1 could indicate a "mild" level, which indicates that the individual shows obsessive thoughts or tendencies that occasionally impair social performance. The individual may spend less than one hour or day occupied with obsessive thoughts. The individual may also try to resist obsessive thoughts or tendencies most of the time and is usually able to stop or divert obsessions with some effort and concentration. The individual may also have long symptom free intervals (e.g., more than 8 consecutive hours per day of being symptom free).

A value of 2 could indicate a "moderate" level, which indicates that the individual shows obsessive thoughts or tendencies that often impair social performance. The individual may spend 12 hours per day occupied with obsessive thoughts. The individual may make some effort to resist obsessive thoughts or tendencies and is sometimes able to stop or divert obsessions. The individual may experience moderately long periods of symptom free intervals (e.g., more than 5 and up to 8 hours per day).

A value of 3 could indicate a "significant" level, which indicates that the individual shows obsessive thoughts or tendencies that usually impair social performance. The individual may spend 3-5 hours per day occupied with obsessive thoughts. Sometimes the individual makes some effort to resist obsessive thoughts or tendencies and is occasionally able to stop or divert obsessions. The individual may be symptom free for intervals that last more than 3 and up to 5 hours per day.

A value of 4 could indicate a "severe" level, which indicates that the individual shows obsessive thoughts or tendencies that cause severe impairment in social performance. The individual may spend 5-7 hours per day occupied with obsessive thoughts. The individual probably yields to all obsessions without attempting to control them, but does so with some reluctance. The individual may rarely succeed to stop obsessions and can only divert attention with difficulty. The individual may experience brief symptom-free intervals (e.g., 1 to 3 consecutive hours per day of being symptom-free).

A value of 5 could indicate a "profound" level, which indicates that the individual is incapacitated due to obsessive thoughts or tendencies. The individual spends more than 8 hours per day occupied with obsessive thoughts, and completely and willingly yields to all obsessions. The individual is rarely able to even momentarily divert thinking. For example, the individual may have less than 1 consecutive hour per day of being symptom free.

A metric for hyperactivity or impulsivity could be given a value on a scale of 1 to 5. Examples of factors that contribute to this metric may include that the individual often fidgets or taps hands or feet or squirms in his/her seat, often leaves his/her seat in situations when remaining seated is expected, often runs about or climbs in situations where it is inappropriate (in adolescents or adults, this may be limited to feeling restless), is often unable to play or engage in leisure activities quietly, is often "on the go" and is unable to be or comfortable being still for extended period of time, often talks excessively, often blurts out an answer before a question has been completed, often has difficulty waiting for his/her turn, and/or often interrupts or intrudes on others.

A value of 1 could indicate a "mild" level, which indicates that the individual presents few, if any, symptoms, and symptoms result in no more than minor impairments in social or occupational functioning. A value of 3 could indicate a "significant" level, which indicates that the individual presents a number of symptoms, intensity of symptoms, and/or functional impairment that are between those specified for "mild" and "profound." A value of 5 could indicate a "profound" level, which indicates that the individual presents several symptoms that are particularly severe, or the symptoms result in marked impairment in social or occupational functioning. In some embodiments, there are no 2 or 4 levels or those levels are analogous to levels described above with reference to other metrics.

A metric for poor attention span or distractible could be given a value on a scale of 1 to 5. Examples of factors that contribute to this metric may include that the individual often fails to give close attention to details, often has difficulty sustaining attention in tasks or play activities, often does not seem to listen when spoken to directly, often does not follow through on instructions and fails to finish duties, often has difficulty organizing tasks and activities, often avoids or is reluctant to engage in tasks that require sustained mental effort, often loses things necessary for tasks, is often easily distracted by extraneous stimuli, and/or is often forgetful in daily activities.

A value of 1 could indicate a "mild" level, which indicates that the individual presents few, if any, symptoms and the symptoms result in no more than minor impairments in social or occupational functioning. A value of 3 could indicate a "significant" level, which indicates that the individual presents a number of symptoms, intensity of symptoms, and/or functional impairment are between those specified for "mild" and "profound." A value of 5 could indicate a "profound" level, which indicates that the individual presents several symptoms that result in marked impairment in social or occupational functioning. In some embodiments, there are no 2 or 4 levels or those levels are analogous to levels described above with reference to other metrics.

A metric for aggression could be given a value on a scale of 1 to 5. A value of 1 could indicate a "mild" level, which indicates that the individual occasionally expresses shouting, mild insults, and curses. A value of 2 could indicate a "moderate" level, which indicates that the individual shouts, curses angrily, and/or makes personal insults. The individual may also express an outward physical aggression that can take the form of slamming doors, ripping clothing, making menacing gestures, or swinging at others. The individual can also express auto-aggression that can take the form of picking/scratching at skin, pulling at hair, or hitting him/herself without inflicting physical harm.

A value of 3 could indicate a "significant" level, which indicates that the individual curses viciously, is extremely insulting and has temper outbursts. The individual may also express outward physical aggression that can take the form of throwing objects down, kicking objects, striking, scratching and pushing others (without inflicting physical harm). The individual may present auto-aggression that can take the form of banging his/her head and firsts into walls, or throwing him/herself onto floor.

A value of 4 could indicate a "severe" level, which indicates that the individual impulsively threatens violence toward others or him/herself. The individual expresses outward physical aggression that may take the form of breaking objects, smashing windows, attacking others and causing mild injury such as bruises or sprains. The individual may also present auto-aggression that can take the form of inflicting minor cuts, bruises, burns, or welts on him/herself.

A value of 5 could indicate a "profound" level, which indicates that the individual threatens violence toward others or him/herself repeatedly and deliberately. The individual may express an outward aggression that can take the form of setting fires, throwing objects dangerously, attacking others and causing serious injury. The individual may also present auto-aggression that can take the form of inflicting major injury on him/herself or a suicide attempt.

A metric for self-injury could be given a value on a scale of 1 to 5. A value of 1 could indicate a "mild" level, which indicates self-injury by an individual that acts with little known expressed urge to self-injure. A value of 2 could indicate a "moderate" level, which indicates that self-injurious acts by an individual or has repeatedly reported urges to self-injure. A value of 3 could indicate a "significant" level, which indicates self-injurious acts by using a single method and not requiring surgical treatment (other than cosmetic). A value of 4 could indicate a "severe" level, which indicates a self-injurious act by an individual that does not require surgical treatment. Lastly, a value of 5 could indicate a "profound" level, which indicates that the individual performed self-injurious acts. In some embodiments, a scale for any of the disclosed metrics could range from other values (e.g., 0 to 5) and include incremental degrees such as a "4+" or "3−."

A metric for tantrums could be given a value on a scale of 1 to 5. The degrees of differences can include a "mild" level that indicate acts by the individual involving holding breath, stamping feet, screaming, or crying, where the individual is reasonably responsive to attempts to calm the individual down; a "moderate" level may indicate breaking things in addition to the mild level factors, where the individual has a limited response to attempts to calm the individual down; a "severe" level indicates biting, kicking, hitting, and threats to hurt someone in addition to the mild level factors, where the individual is not responsive to attempts to calm the individual down.

The levels for the tantrums metric could also reflect a frequency of tantrums. For example, a value of 1 could reflect a "mild" level where tantrums occurred rarely or not at all, a value of 2 could reflect a "moderate" level where mild to moderate tantrums occurred more than once, a value of 3 could reflect a "significant" level where mild to moderate tantrums occurred 3+ times, a value of 4 could reflect a "severe" level where moderate to severe tantrums occurred 3+ times, and a value of 5 could reflect a "profound" level where severe tantrums occur multiple times per day.

An metric for irritability could be given a value on a scale of 1 to 5. The symptoms may include the individual's "behavior," which is characterized by at least four symptoms exhibited during interactions with at least one individual who is not a sibling. Examples of the symptoms include that the individual may often lose his/her temper, is often touchy or easily annoyed, or is often angry and resentful. A value of 1 could indicate a "mild" level where symptoms are confined to only one setting, a value of 3 could indicate a "significant" level where some symptoms are present in at least two settings, and a value of 5 could indicate a "profound" level where some symptoms are present in three or more settings, etc.

A metric for non-compliance could be given a value on a scale of 1 to 5. Examples of factors that influence this metric include whether the individual argues with authority figures, defies or refuses to comply with requests from authority figures, deliberately annoys others, and blames others for his/her mistakes or misbehavior. A value of 1 could indicate a "mild" level where symptoms are confined to only one setting, a value of 3 could indicate a "significant" level where some symptoms are present in at least two settings, a value of 5 could indicate a "profound" level where some symptoms are present in three or more settings.

A metric for sleep disorder could be given a value on a scale of 1 to 5. Examples of symptoms include difficulty initiating sleep; difficulty maintaining sleep, characterized by frequent awakenings or problems returning to sleep after awakenings; early morning awakening with inability to return to sleep; or a sleep disturbance that causes clinically significant distress or impairment in important areas of functioning. A value of 1 could indicate a "recurrent" episode where two or more episodes occur within the space of 1 year. A value of 2 could indicate "episodic" symptoms that last at least 1 month but not less than 3 months. Lastly, a value of 3 could indicate "persistent" symptoms that last 3 or more months.

A metric for anxiety could be given a value on a scale of 1 to 5. Examples of symptoms include feelings of nervousness, anxiety, being on edge; not being able to stop or control worrying; worrying too much about different things; trouble relaxing; being so restless it is hard to sit still; being easily annoyed/irritable; and feeling afraid as if something bad is going to happen.

A metric for separation anxiety could be given a value on a scale of 1 to 5. Examples of symptoms include recurrent excessive distress when anticipating or experiencing separation from home or from major attachment figures; persistent and excessive worry about losing major attachment figures or about possible harm to them, such as illness, injury, disasters or death; persistent and excessive worry about experiencing an untoward event that causes separation from a major attachment figure; persistent reluctance or refusal to go out, away from home etc. for fear of separation; persistent and excessive fear of or reluctance of being alone or without major attachment figures at home or in other settings; persistent reluctance or refusal to sleep away from home or to go to sleep without being near a major attachment figure; repeated nightmares involving the theme of separation; and repeated complaints of physical symptoms when separation from major attachment figures occurs or is anticipated.

For either the anxiety metric or the separation anxiety metric, a value of 1 could indicate a "mild" level where the individual shows symptoms 0-1 times throughout the day; a value of 2 could indicate a "moderate" level where the individual shows symptoms 2-3 times throughout the day, a value of 3 could indicate a "significant" level where the individual shows symptoms 3-4 times throughout the day, a value of 4 could indicate a "severe" level where the individual shows symptoms most of the day, and a value of 5 could indicate a "profound" level where the individual shows symptoms frequently, all the time, or consistently.

A metric for social withdrawal could be given a value on a scale of 1 to 5. For example, a value of 1 could indicate a "mild" level that indicates an individual is hesitant to engage/interact in social (potentially unknown) environments. A value of 3 could indicate "significant" level that indicates an individual is reluctant to engage in most activities. A value of 5 could indicate a "profound" level that indicates an individual does not want to engage in any activities including interaction with close friends and family, etc.

A metric for fearfulness or worry could be given a value on a scale of 1 to 5. For example, a value of 1 could indicate a "mild" level that indicates that an individual has a general fear of one or more triggers that are typically not present. A value of 3 could indicate "significant" level that indicates an individual has fear of one or more triggers that causes significant response. A value of 5 could indicate a "profound" level that indicates an individual has a debilitating fear of one or more triggers.

A metric for depression could be given a value on a scale of 1 to 5. Examples of symptoms include a depressed mood most of the day nearly every day; markedly diminished interest or pleasure in activities; significant weight loss; insomnia or hypersomnia; psychomotor agitation or retardation; fatigue or loss of energy; feelings of worthlessness or excessive and inappropriate guilt; diminished ability to think or concentrate, indecisiveness; recurrent thoughts of death.

For example, a value of 1 could indicate a "mild" level where an individual presents few, if any, symptoms where the intensity of a symptom is distressing but manageable, and the symptoms resulted in minor impairment in social or occupational functioning. A value of 3 could indicate a "moderate" level where the number of symptoms, intensity of symptoms, and/or functional impairment are between "mild" and "profound." A value of 5 could indicate a "profound" level where the number of symptoms and the intensity of the symptoms constitute seriously distressing and unmanageable levels, and the symptoms markedly interfere with social and occupational functioning, etc.

A metric for sadness could be given a value on a scale of 1 to 5. For example, a value of 1 could indicate a "mild" level that indicates a general lack of joy in everyday activities. The sadness is hard to detect by relations that are not close to the individual. A value of 3 could indicate a "moderate" level that indicates an individual gets upset easily (e.g., crying very often), seemingly for no apparent reason. A value of 5 could indicate a "profound" level that indicates an individual experiences frequent episodes of crying, decrease in energy, lack of engagement under normal circumstances. The individual at this level generally cannot be consoled.

A metric for lethargy could be given a value on a scale of 1 to 5. For example, a value of 1 could indicate a "mild" level that indicates an occasional loss of energy/motivation that sometimes lasts for an abnormal period of time. The lethargy can be fought off with slight moderate of effort. A value of 3 could indicate a "moderate" level that indicates drowsiness or slowing of thoughts or loss of energy that lasts for an abnormal period of time and can only be fought off with moderate to significant effort. A value of 5 could indicate a "profound" level that indicates a severe drowsiness/slowing of thoughts/loss of energy in which the patient can be aroused by moderate stimuli and then drift back to sleep.

The metrics used to assess a patient could also be given binary values such as Yes/No. Examples of these metrics include whether an individual is experiencing chronic constipation, frequent diarrhea, acid reflux, hay fever or asthma, and the like. The metrics used to assess a patient could also include multiple selectable options such as food allergies that can include any of gluten, dairy, nuts, or others. A metric for picky eating could have a Yes/No binary option followed by mild, moderate, or severe options. Other examples include a metric for a change in appetite that includes options indicating a decrease or increase in appetite; a metric for extreme sensitivity to sensory input with a Yes/No option followed by selectable noise, light, smell, and texture options; a metric for migraines with multiple selectable options such as mild, moderate, or severe, followed by a selectable frequency of daily, weekly, monthly, or occasional; a metric indicating whether an individual has a phobia with a Yes/No option followed by multiple selectable options; a metric for bed wetting; and a metric for whether the individual experiences gender dysphoria (e.g., where the individual exhibits a marked difference between the individual's expressed/experienced gender and the gender that others would assign to the individual, or it must continue for at least six months). There are various other examples of metrics used to assess an individual that are not described herein but could be understood based on this disclosure.

Figure 2:
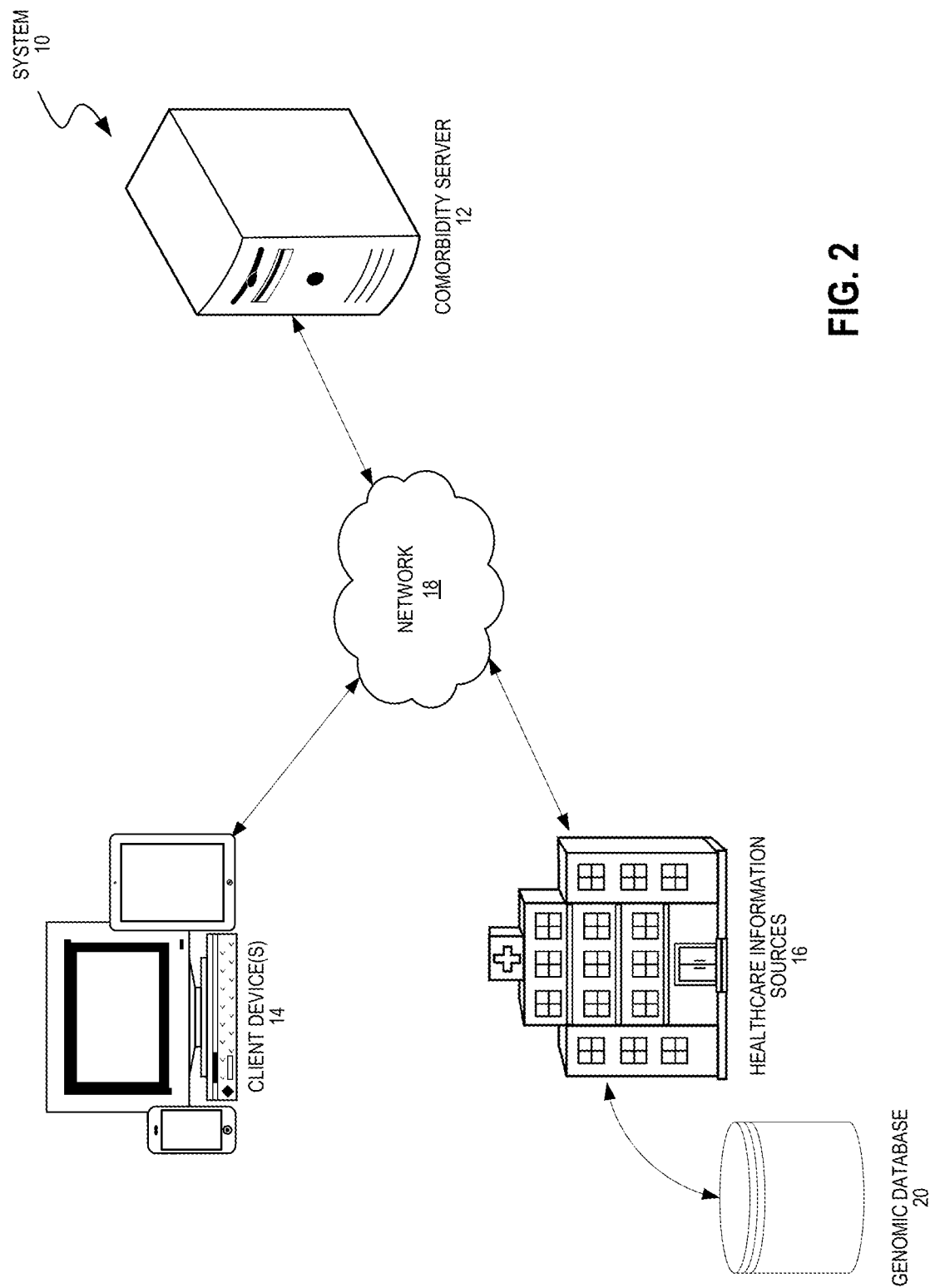
FIG. 2 is a block diagram illustrating a platform for assessing and treating individuals according to some embodiments of the present disclosure.

FIG. 2 is a block diagram illustrating the comorbidity-based healthcare computer system 10 implementing the disclosed platform according to some embodiments of the present disclosure. The system 10 can build individual profiles for individual patients and generate comorbidity profiles based on data obtained from communities of users and a number of patient profiles. The comorbidity profiles can be used to assess and treat patients, and a service of the system 10 can monitor and track patient progress to improve the operation of the platform.

The system 10 includes components such as a comorbidity server 12, client devices 14, and healthcare information sources 16, all interconnected over a network 18 such as the Internet. In some embodiments, the system 10 can include a genomic database 20, which includes patient genome information. A genome is the entire DNA content that is present within one cell of a patient. Genetic mapping can be performed on genomes to identify DNA sequences including markers of specific diseases or conditions. As such, partial DNA sequences ("targets") can be analyzed to detect the markers of diseases or conditions in other patients.

The network 18 may include any combination of private, public, wired, or wireless portions. The data communicated over the network 18 may be encrypted or unencrypted at various locations or along different portions of the network 18. Each component of the system 10 may include combinations of hardware and/or software to process data, perform functions, communicate over the network 18, and the like. For example, a component of the system 10 may include a processor, memory or storage, a network transceiver, a display, an operating system and application software (e.g., for providing a user interface), and the like. Other components, hardware, and/or software included in the system 10 that are well known to persons skilled in the art are not shown or discussed herein for brevity.

Examples of the devices of the system 10 could include mobile phones, wearables, remote monitoring biometric sensors, as well as environmental sensors used in a house such as NEST devices, and video/voice devices. The devices of the system 10 can also belong to medical systems that a client might be wearing for data collection and data transmission purposes and intervention purposes. In some embodiments, there are also other sources of data that do not include a device but are only data sources of environmental factors such as air quality index or pollen measurement technologies.

For example, the client devices 14 (also referred to individually as client device 14) are used by users to interact with the system 10. Examples of the client devices 14 include smart phones (e.g., APPLE IPHONE, SAMSUNG GALAXY, NOKIA LUMINA), tablet computers (e.g., APPLE IPAD, SAMSUNG NOTE, AMAZON FIRE, MICROSOFT SURFACE), computers (e.g., APPLE MACBOOK, LENOVO 440), and any other device that is capable of accessing information provided by the comorbidity server 12 over the network 18. The client device 14 may run a mobile application ("app") used to interact with the comorbidity server 12 over the network 18. The mobile app may be downloadable from an app store or equivalent app library.

In the illustrated example, the comorbidity server 12 includes any number of server computer systems that can build patient profiles to track the patients and discover their comorbidities. The comorbidity server 12 may collect healthcare-generated information over the network 18 from the healthcare information sources 16 for building the patient profiles and comorbidity profiles to assess and treat patients. Accordingly, information about comorbidities and patient services can be provided by the comorbidity server 12 over the network 18 to the client devices 14.

The healthcare information sources 16 may include any number of servers or other computing devices that can collect, store, and/or provide healthcare-related information to the comorbidity server 12 over the network 18. For example, the healthcare information sources 16 may include any healthcare provider such as medical facilities, private offices, or devices administered by healthcare professionals. In some embodiments, the healthcare information may include at least portions of medical records utilized for discovering comorbidities and identifying suitable treatments, as detailed below.

In some embodiments, the comorbidity server 12 may provide or administer a portal that allows healthcare consumers to access a library of information related to the comorbidities and patient services. Examples of the portal include a website, a mobile app, or any communication channels for providing information about comorbidity related information and services to the client devices 14. As such, the system 10 enables users of the client devices 14 to interact with the comorbidity server 12 to upload information used to build patient profiles and enables tracking the patients' progress, diagnosing comorbidities, and recommending suitable treatments.

The system 10 incorporates information and data from various sources to build individual patient profiles used to track patients and generate comorbidity profiles. For example, the system 10 can synthesize numerous patient profiles to generate the comorbidity profiles subsequently used to assess patients as having particular comorbidities. Treatments can then be prescribed based on the comorbidity profiles.

Hence, the system 10 can enable healthcare professionals to identify treatments for patient profiles classified with comorbidities, rather than prescribing a piecemeal combination of treatments for separate and distinct known diseases or conditions. Moreover, since the patient profile itself can be thought of as a multidimensional representation of a combination of known and unknown diseases or conditions, the system 10 enables healthcare professionals to effectively treat unknown diseases or conditions as well as known diseases or conditions.

For example, in the context of known diseases or conditions, almost all patients with autism have comorbidities. A patient's profile may indicate that the patient has autism in combination with numerous physical diseases such as hypothyroidism, seizures, etc. The patient can be classified as having a particular comorbidity profile based on the patient profile, and treatments that are suitable for that comorbidity profile can be prescribed to the patient. As such, a healthcare professional can treat patients for the simultaneous presence of multiple known or unknown diseases or conditions rather than prescribing a piecemeal combination of treatments for separate and distinct known diseases or conditions that affect the patient.

Although the disclosed embodiments generally describe an implementation to assess and treat autism, the disclosed technology is not so limited. Instead, the disclosed technology can be implemented to diagnose and treat an expansive range of diseases or conditions including ADHD, Fragile X, 22q11 deletion syndrome, anxiety and anxiety disorders, depression, Tic disorder, Tourette Syndrome, and others known to person skilled in the art but omitted herein for brevity.

Figure 3:
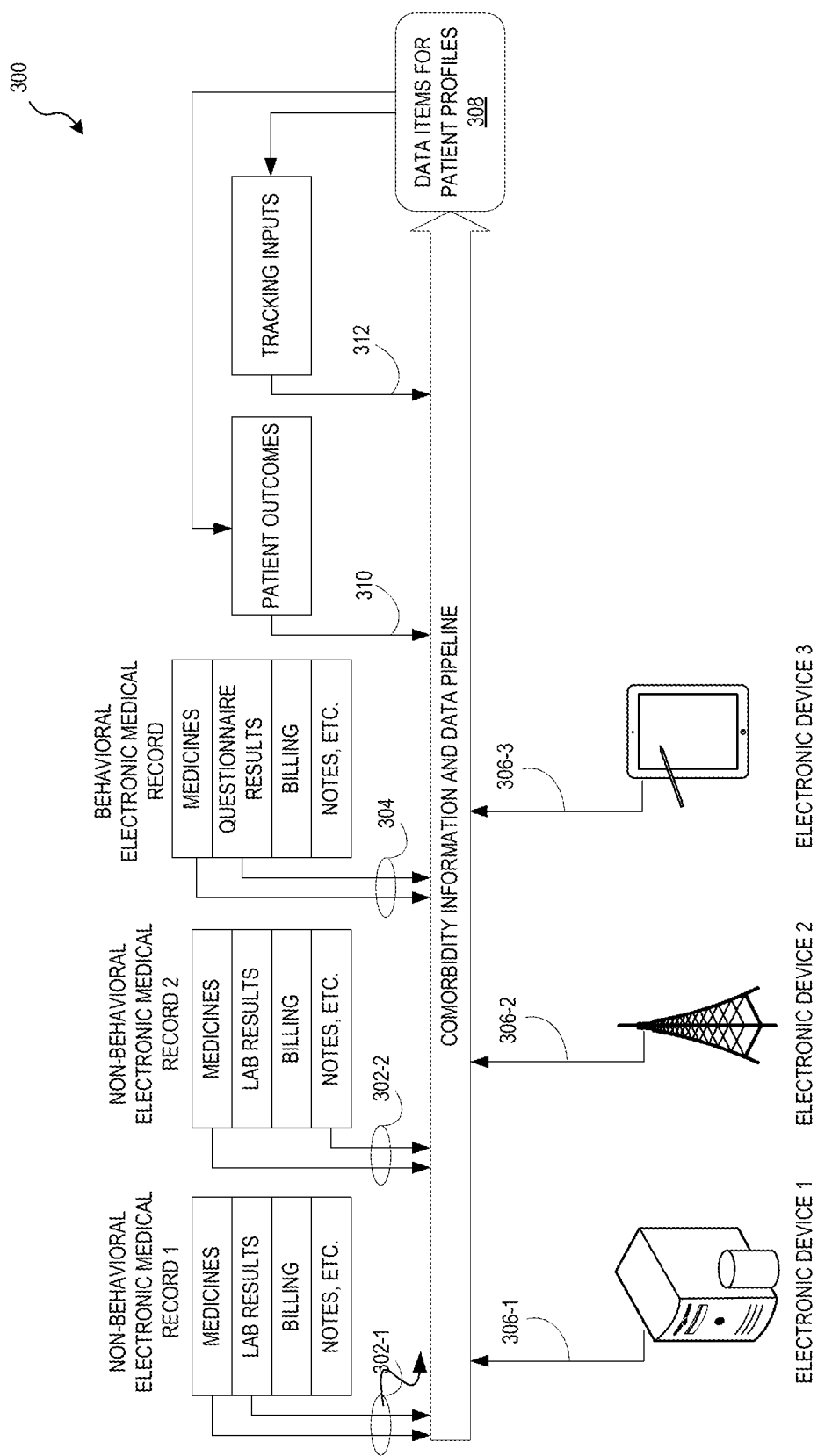
FIG. 3 depicts an information pipeline for the platform according to some embodiments of the present disclosure.

FIG. 3 depicts a comorbidity information and data pipeline for the system 10 according to some embodiments of the present disclosure. The comorbidity pipeline 300 represents communication channels (e.g., of network 18) and devices (e.g., client devices 14 or other sources) operating as sources of data used to build the patient profiles. The sources may include healthcare facilities, providers, or related entities that store or generate healthcare information or data. For example, the healthcare information sources 16 can generate and store EMRs for patients. Data contained in the EMRs can be sent over the network 18 to the comorbidity server 12 to build the patient profiles. In some embodiments, EMR data that is sent over to the network is done in partnership with other companies that have developed a technology to create communication with EMRs.

For example, the comorbidity pipeline 300 can collect data items 302-1 such as prescribed medicines or lab results extracted from a non-behavioral EMR, which is a record of diseases or conditions that are not behavioral in nature (e.g., gastrointestinal disease). The comorbidity pipeline 300 can also collect data items 302-2 extracted from another non-behavioral EMR. The data items 302-2 can be different from the data items 302-1. The comorbidity pipeline 300 can also collect data items 304 from a behavioral EMR, which is a record for behavioral diseases or conditions. Various types of data can be collected by the comorbidity pipeline 300 from a variety of sources.

Other sources of data for the patient profiles may include computing devices that are not necessarily related to healthcare services. For example, the comorbidity pipeline 300 can collect data items 306 from diverse electronic devices including server computer systems, sensor systems, and the client devices 14. In particular, data items 306-1 may relate to risk factors such as demographic data or socioeconomic data from public databases. The data items 306-2 may be collected from sensors (e.g., on a tower) that generates data about environmental risk factors in a location where a patient lives. The environmental risk factors may include, for example, air or water quality.

The data items 306-3 can include user-selected data item values selected on a graphical user interface (GUI) rendered on a mobile device. The values of the user-selected data items can be responsive to preset questions presented to the user on the GUI of the mobile device. This disclosure includes examples of the present questions and user-selectable answers. The preset questions may include 100-300 questions of a healthcare questionnaire that is presented to the user on the GUI. For example, the GUI of a mobile app running on the client device 14 may include user-selectable controls that enable a user to enter data items as binary values or values within a range of predetermined values in response to preset questions. For example, a graphical control object may include a slider bar that has a scale ranging from 0 to 5. The user can move the slider bar to a value that represents the severity of a particular symptom experienced by a patient. In another example, the user can select a value indicating that the patient has a known disease or condition. In yet another example, the user can input a text value into a field. These data item values 306-3 can be collected into the comorbidity pipeline to build the patient profile.

A customized patient data category can also be created by the client or user. That is, the mobile app has content that is pre-defined, but every page and every category has the ability to accept content from the user that is not included in the predetermined list. The customized content can become part of system's standard content if more than a minimum number of individuals (e.g., 3 people) add the same customized content.

The data items collected into the comorbidity pipeline 300 from the various disparate sources collectively form the data items 308 for patient profiles. For example, the data items 308 for patients can be received by the comorbidity server 12, transformed into a common format, and stored in records that represent patient profiles. In some embodiments, a user can access a patient profile to view and modify its contents. For example, a caregiver using the client device 14 may access a patient profile to update data item values. In another example, a doctor may access a patient profile from a computer at a hospital to update the contents of the patient profile. As such, a patient profile can be regularly updated to reflect the patient's current state and progress.

The comorbidity pipeline 300 may be part of a service to track patient progress and provide timely information to patients or caregivers. For example, data items 310 can reflect a patient's outcomes relative to prescribed treatments noted in the patient's profile. As such, the data items 310 can be used by the comorbidity server 12 to determine whether treatments are effective or ineffective.

In some embodiments, data items 312 can be collected by the comorbidity pipeline 300 periodically (e.g., hourly or daily) to track a patient's progress. For example, the comorbidity server 12 may administer an interactive portal that prompts a user for periodic inputs. The data item values may indicate an ongoing severity of symptoms experienced by the patient. These periodic inputs can be used to update the patient's profile.

In some embodiments, the data items 312 can be used for compliance monitoring. For example, the mobile app may prompt the user to input whether the patient is complying with a treatment, such as regularly consuming medicine. Tracking a patient's compliance in combination with data about the patient's outcomes can be used to determine whether prescribed treatments are effective at relieving a patient's symptoms.

In some embodiments, the data items 312 can be used to alert caregivers of the patient's failure to comply. For example, upon receiving an input at the client device 14 about a patient's noncompliance or after a designated period of time has elapsed without receiving confirmation of the patient's compliance, the comorbidity server 12 may issue a notification to a caregiver's electronic account about the patient's noncompliance. The notice can be used to alert the caregiver to take action when compliance is critical.

The type of data items and their sources are not limited to the examples described above. Instead, these examples are illustrative of the diverse types of data and sources that can be employed to collect data into the comorbidity pipeline 300 to build a patient profile. Unlike conventional systems that collect minimally sufficient information about a patient to identify treatments based on known diseases or conditions, the disclosed technology makes use of diverse data types from diverse sources to identify treatments customized for a patient's profile rather than a particular disease or condition.

Figure 4:
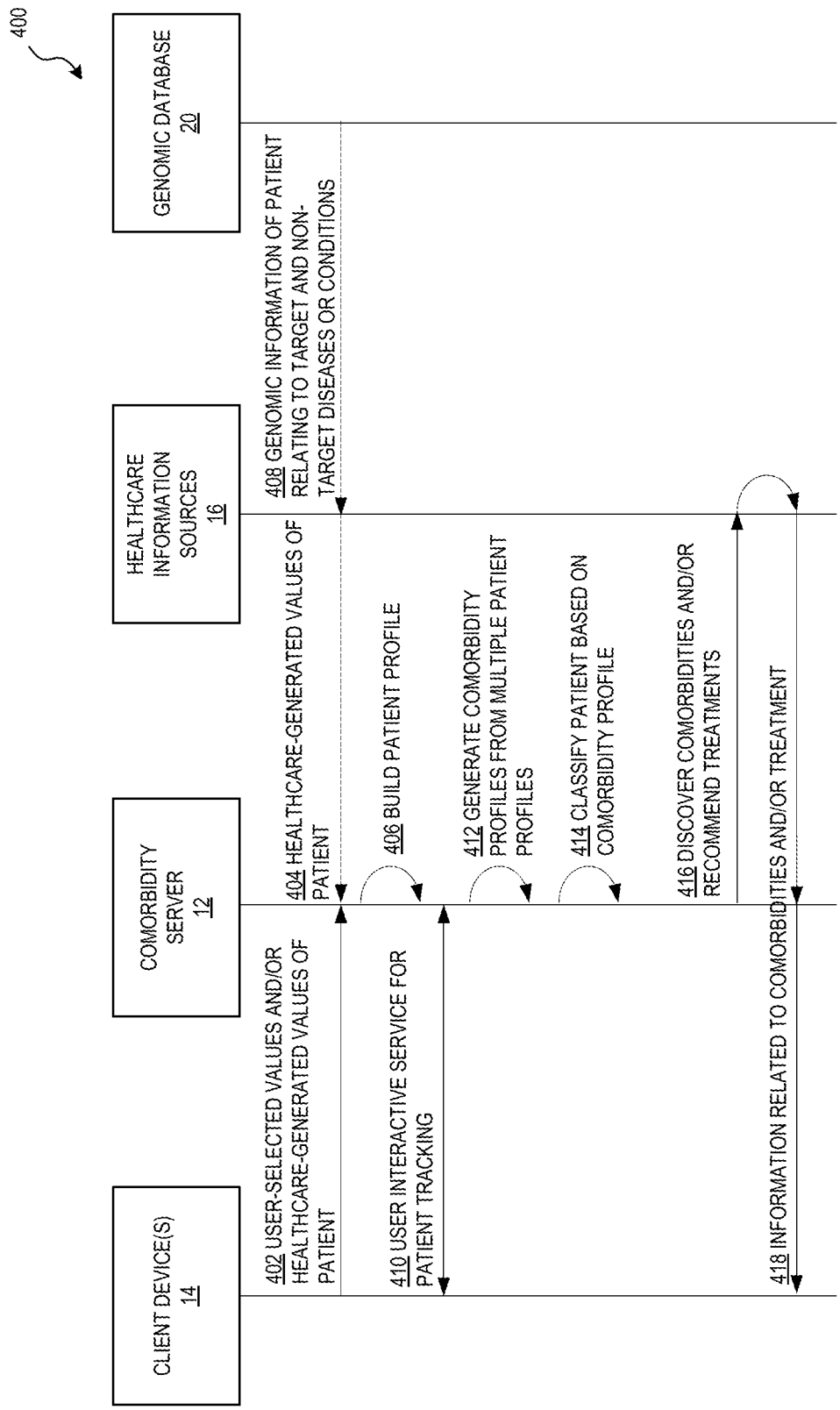
FIG. 4 is a sequence diagram illustrating a process of the platform according to some embodiments of the present disclosure.

FIG. 4 is a sequence diagram that illustrates a process of the system 10 according to some embodiments of the present disclosure. The illustrated process 400 generally includes steps for building patient profiles, tracking patients, and generating comorbidity profiles used to identify treatments. For example, the process 400 can begin by collecting data item values into the comorbidity pipeline 300 and communicating the data item values over the network 18 to the comorbidity server 12.

In particular, in step 402, the comorbidity server 12 can receive user-selected data item values over the network 18 from the client device 14. For example, each user-selected data item value can be selected by a user of the client device 14 to indicate a severity of a symptom experienced by a patient. In some embodiments, the severity value may be selected from a predetermined range such as 1, 2, 3, 4, or 5, where 1 indicates low severity and 5 indicates high severity. In some embodiments, the predetermined range can be selected from a continuous range of 1 through 5 rather than discrete values.

In step 404, the comorbidity server 12 may receive healthcare-generated data item values over the network 18 from the healthcare information sources 16. For example, the healthcare-generated data items may relate to a disease or condition unrelated to the user-selected data values. In some embodiments, some or all of the healthcare-generated data item values can be received by the comorbidity server 12 from the client device 14 rather than from the healthcare information sources 16. For example, a user can enter data on a mobile app of the client device 14 to indicate that the patient has been diagnosed with a particular disease or condition.

In step 406, the comorbidity server 12 builds the patient's profile based on the combination of user-selected data item values and the healthcare-generated data item values. For example, the received data item values can be synthesized into a single record that represents a multidimensional patient profile. The patient profile can enable a user to access services administered by the comorbidity server 12. For example, the comorbidity server 12 can administer a network portal (e.g., a website) or provide interactive services through a mobile app running on the client device 14. The services can be used to update the patient's profile and receive feedback from the comorbidity server 12.

In some embodiments, the data item values received by the comorbidity server 12 can be adjusted so that the patient's profile reflects values relative to other patient profiles. For example, the user-selected data values can be adjusted with respect to the patient's age and gender, or relative to numerous other patient profiles.

In some embodiments, the healthcare-generated data item values may include genomic information from the genomic database 20. The genomic information can include the patient's entire genome or portions of the genome. For example, in step 408, genomic information may be sent over the network 18 to the healthcare information sources 16 or directly to the comorbidity server 12. In some embodiments, a user of the client device 14 can input or upload the patient's genomic information.

The portions of the genome can include non-target DNA sequences, which are not related to any known diseases or conditions associated with the patient. In some embodiments, the portions of the genome can include target DNA sequences. In some embodiments, the genomic information can include both target and non-target DNA sequences. For example, the genomic information can include the patient's entire genome. Incorporating target or non-target portions of the patient's genome into the patient's profile adds additional data points to improve discovery of treatments for unknown diseases or conditions.

In some embodiments, the healthcare-generated data items of the patient may include risk factors. A computing device can send risk factor data item values associated with the patient over the computer network to the comorbidity server 12. The risk factor data item values can be actively or passively collected by the computing device. For example, actively collected risk factors input to the client device 14 may include the patient's lifestyle (e.g., eating and exercise habits). The passively collected risk factors may include data collected passively from sensors. As such, the patient's profile can be built based on the risk factor values and/or genomic information in addition to the user-selected data values and the healthcare-generated values.

In step 410, the comorbidity server 12 provides an interactive service to track the patient's progress, including outcomes and compliance. For example, the service may prompt the user of the client device 14 to provide periodic data item values over the network 18 to the comorbidity server 12. The periodic data may include hourly or daily severity values of symptoms. The comorbidity server 12 may respond to the periodic values with feedback data sent to the client device 14.

The disclosed technology identifies treatments from patient profiles based on comorbidities rather than separate and distinct diseases or conditions. In particular, the comorbidity server 12 can build patient profiles for numerous patients. In step 412, the comorbidity server 12 can process the patient profiles to generate multiple comorbidity profiles. The comorbidity profiles can be generated from the patient profiles by using a variety of techniques.

For example, an Apriori algorithm can be used to identify patterns that define the comorbidity profiles. Specifically, combinations of data items such as genetics, symptoms, and diagnosis obtained from patient profiles can be input into the Apriori algorithm. The system 10 can determine the co-occurrence of genetic mutations based on the genetic information, can determine the co-occurrence of symptoms based on the symptom and diagnosis information, and can discover relationships between genetic mutations and certain symptoms or diagnoses based on the combination of all the data items. In another example, a hotspot algorithm can be used to pinpoint subsets of patient profiles that benefit from specific treatments (e.g., medications). The outputs of the hotspot algorithm can be used in part to define the comorbidity profiles.

In some embodiments, the comorbidity server 12 can apply a clustering algorithm to partition the patient profiles into clusters, where each cluster represents a comorbidity profile. Specifically, the comorbidity server 12 can embed patterns of data items as points in an N-dimensional space, where each dimension may represent, for example, outputs of an Apriori algorithm. The number of clusters formed from patient profiles can be preset or defined by a minimum and/or maximum number of patient profiles that can be included in any cluster. For example, a cluster may be defined automatically from a population of at least 100,000 patient profiles but not more than 1,000,000 profiles.

The clustering algorithm could automatically group patient profiles into clusters that may be mutually exclusive or could overlap. Details about clustering are well known to persons skilled in the art and, as such, are omitted herein. Notably, the disclosure is not limited to any of the aforementioned algorithms to generate comorbidity profiles. Instead, any approach could be utilized to generate the comorbidity profiles. Moreover, in some embodiments, expert medical knowledge can be used to label the comorbidity profiles to have medically significant meanings.

The system 10 can also determine causal relationships within and across dimensions of the patient profiles. For example, the system 10 can implement a causality algorithm to discover relationship between treatments (e.g., medications, supplements, diets, and therapies) and symptoms. In particular, causality relationships can be readily discovered because the system 10 tracks outcome data. In some embodiments, the causality algorithm can use a Bayesian Network to determine the causal relationships.

In step 414, the patient profile is classified as belonging to one or more of the comorbidity profiles to receive recommendations for corresponding treatments. However, unlike conventional methods, the specific combination of diseases or conditions in a comorbidity profile may be unknown. That is, each comorbidity profile is based on the data collected from the comorbidity profile, and treatments for that profile are not necessarily associated with any specific known or unknown disease or condition.

In some embodiments, each comorbidity profile can include a vector of scores, each corresponding to the "fitness" of a treatment to a patient. The system 10 can recommend treatments with the highest fitness scores to a patient based on the patient's associated comorbidity profile. To derive the "fitness" scores, various data mining algorithms may be used, including variants of regression algorithms and ensemble methods such as random forest (RF) or gradient boosting machine (GBM). As such, the interactive service can track changes in periodic data to update the user's profile.

In step 416, the comorbidity server 12 can send a message to the healthcare information sources 16 regarding the comorbidity profiles and/or recommend treatments for the patient based on the comorbidity profile classification of the patient's profile. For example, the comorbidity server 12 may notify the patient's caregiver about the patient's comorbidity profile and recommend corresponding treatments. In step 418, the healthcare information sources 16 can then send information related to the patient's comorbidities to the client device 14 via the comorbidity server 12. Alternatively, the comorbidity server 12 can send the information of the patient's comorbidities and/or treatments directly to the client device 14.

In some embodiments, the disclosed technology can be used to define new diseases or conditions and identify treatments. For example, the comorbidity server 12 can send a comorbidity profile to the healthcare information sources 16, which can label the comorbidity profile as a diseased state with corresponding treatments. Moreover, the disclosed technology can implement a machine learning algorithm using the feedback loops described above to learn of more effective treatments for the comorbidity profiles.

Figure 5:
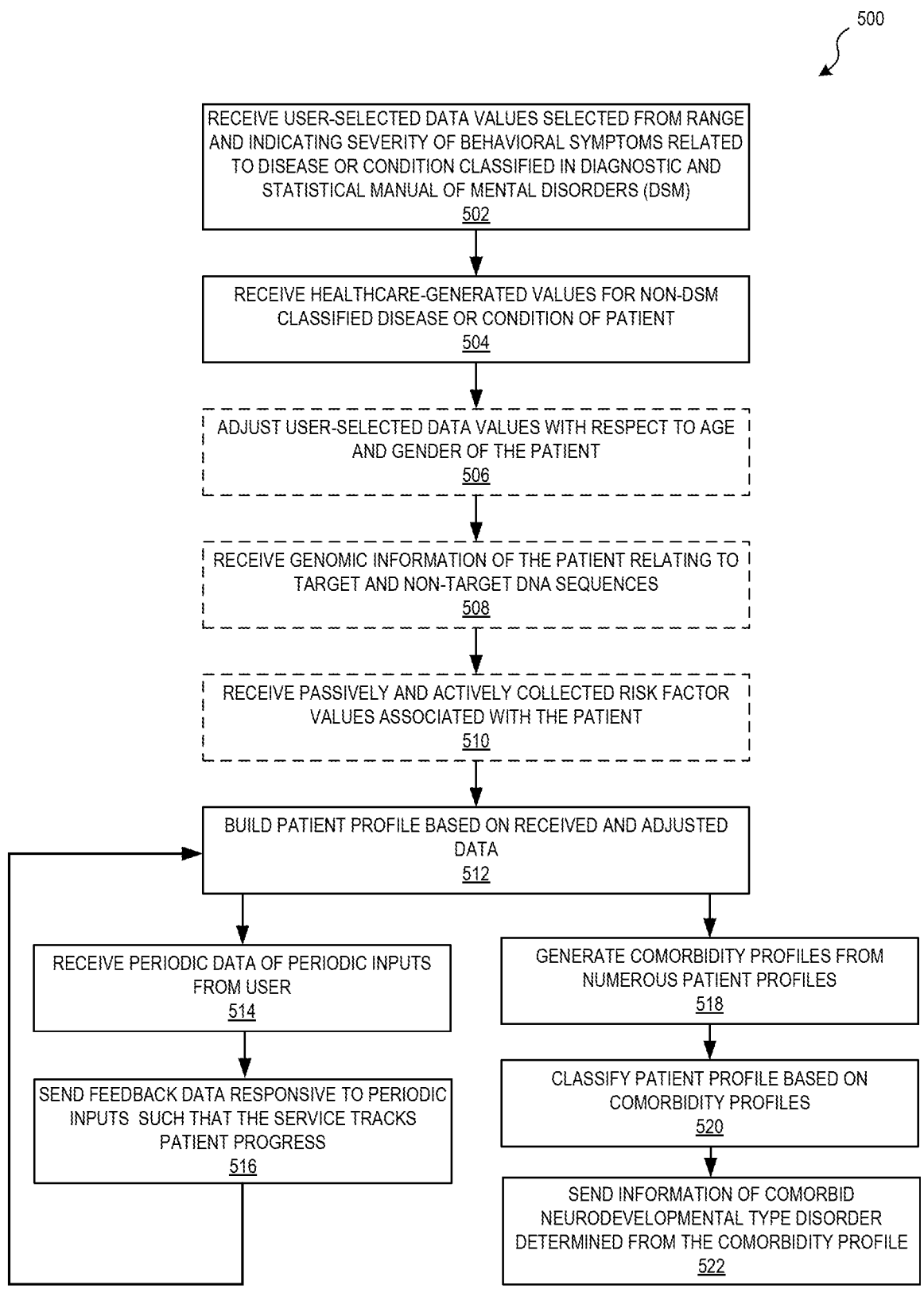
FIG. 5 is a flowchart illustrating a method performed by a server of the platform according to some embodiments of the present disclosure.

FIG. 5 is a flowchart illustrating a method performed by a comorbidity platform server according to some embodiments of the present disclosure. The method 500 illustrates a specific implementation for patients with neurodevelopmental type disorders.

In step 502, the comorbidity server 12 receives user-selected data values selected from a range that indicates values associated with behavioral symptoms related to a classification of diseases or condition. Examples of behavioral symptoms include a sleeping behavior, a repetitive behavior, or a hyperactive behavior.

In step 504, the comorbidity server 12 receives healthcare-generated values associated with diseases or conditions that are not classified in the DSM. Examples include a gastrointestinal disease, seizures, or a thyroid disease. As such, the comorbidity server can use data item values for seemingly unrelated diseases or conditions. The DSM and non-DSM comorbidities can range across many conditions and/or symptoms, which are not limited to gastrointestinal disease, a seizure, or a thyroid disease. Many other conditions can be involved such as diabetes, hypertension, sleep disorder, strep throat, childhood deafness, etc.

In step 506, the comorbidity server 12 may adjust the data item values with respect to the age and gender of the patient. Adjusting the data item value can help compare the patient's profile to other patient profiles.

In some embodiments, the comorbidity server 12 can receive an additional combination of diverse data item values. For example, in step 508, the comorbidity server 12 can receive genomic information including target and/or non-target DNA sequences of the patient. In another example, in step 510, the comorbidity server 12 can receive passively and actively collected risk factor values associated with the patient. The comorbidity server 12 can then build the patient's profile in step 512 based on the received, and possibly adjusted, data item values.

The patient profile can then be used to track the patient's progress and/or classify the patient's profile to diagnose and treat the patient based on comorbidities rather than recommending a piecemeal treatment plan based on distinct and known diseases or conditions. As such, the patient can experience a more customized and effective treatment with ongoing tracking of the patient's progress.

To track the patient's progress, a feedback loop is formed where the comorbidity server 12, in step 514, can receive data indicative of periodic inputs at the client device 14 sent over the network 18 and, in step 516, can send feedback responsive to the periodic inputs. In some embodiments, as described further below, data indicative of a patient's progress is event driven. For example, an event experienced by a patient may generate data that is sent to the comorbidity platform To classify the patient's profile, the comorbidity server 12 generates multiple comorbidity profiles from numerous patient profiles and uses the comorbidity profiles to classify subsequent patient profiles in step 518. In step 520, the comorbidity server 12 classifies the patient's profile based on the comorbidity profiles. For example, the patient's profile can be classified as a particular comorbidity profile that is associated with a neurodevelopmental type disorder such as autism and one or more additional diseases or conditions. Then, in step 522, the comorbidity server 12 can send information about the patient's comorbidity profile including a neurodevelopmental type disorder and additional diseases or conditions. The information may include suitable treatments.

The disclosed embodiments include techniques for assessing or treating patients in respective groups of users. More generally, each patient is a user that belongs to a community of users that collectively monitor and track a patient. In some embodiments, each community includes only one user designated as a patient and one or more users with designated roles that participate in monitoring and/or tracking the patient activities. The non-patient users can utilize devices that are linked to a service that can monitor and track the patient user via the non-patient users. In other words, the service can monitor and track the activity of a user indirectly through the other users in the community that include the monitored and tracked user. In some instances, the service can also monitor and track the patient directly by receiving feedback from the patient via a device linked to the service.

Figure 6:
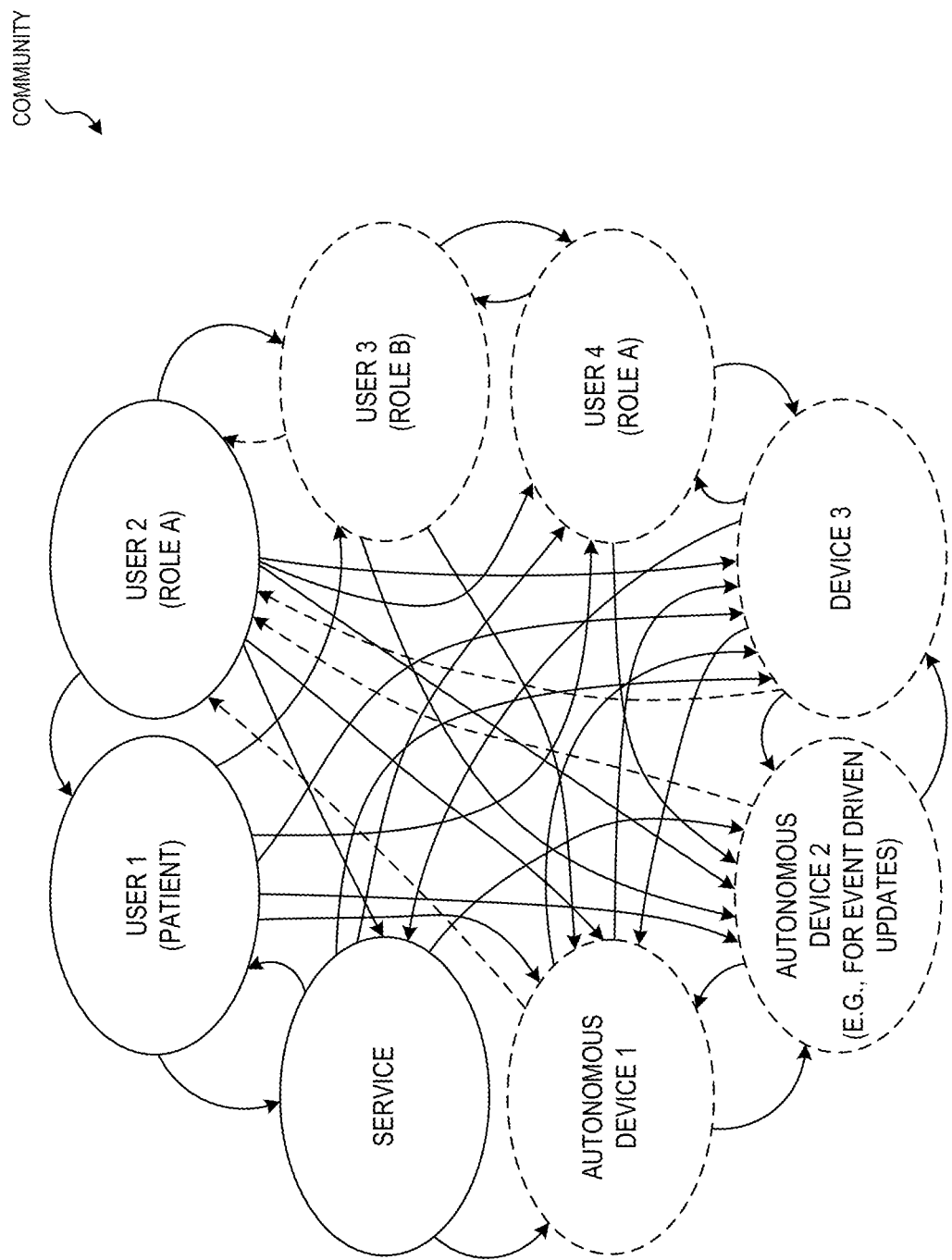
FIG. 6 is a block diagram illustrating a community of resources for assessing and treating a patient according to some embodiments of the present disclosure.

FIG. 6 is a block diagram illustrating a community of resources according to some embodiments of the present disclosure. As shown, a community is depicted as many interconnected nodes involved in collecting or sharing data to assess and treat a patient. The nodes can represent different users that have roles indicating relationships relative to the patient. Examples of roles include caregiver, parent, sibling, relative, or friend. Other examples of roles include primary care physician, specialist, special education teacher, occupational therapist, speech therapist, behavioral therapist, etc. For example, a user role may be a parent or child of the patient. A user with a role may actively input data indicating observations related to the patient's activity. The data may be input or received by the platform periodically to update the patient's profile.

In some embodiments, the patient profile may be updated in response to the occurrence of an event (e.g., incident). For example, nodes can represent autonomous computing devices that passively collect data of the patient's activities and transmit the collected data to the platform. For example, a fitness tracker worn by the patient can passively collect activity data and provide that data to the platform that also collects data actively input by users of the patient's community.

In this way, the platform can monitor or track a patient's behavior indirectly and/or directly from activity data that was actively input by users in the patient's community, passively collected by autonomous devices, and even data actively input by a patient. The platform can collectively use this data to assess the patient and formulate a treatment. For example, the platform can identify a suggested goal for the patient that is implemented by the patient's community (e.g., the patient's family). For example, based on information that the family provides of comorbid symptoms and conditions, the platform can suggest certain goals to the family to improve the quality of life and health of a patient with the conditions. For each goal, the platform can provide content for influencers of the platform and of the suggested goal, and also suggest certain actions that users of the community can take to achieve goals. A user of the community can also define a goal for the user or the patient and suggest actions to progress towards achieving the goal. In some embodiments, the goals and actions are created in a measurable form based on intensity, frequency, duration, or similar measurable units. The platform can track the progress across goals and make suggestions including other actions for users, depending on the level of progress that has been made towards completing the goal. The platform can also identify other symptoms that may be impacted by the goals and suggest actions and continue to update information in the patient's profile accordingly.

In some embodiments, each goal is linked to a symptom and some symptoms are impacted by similar influencers, and may have similar goals associated with them. In some embodiments, the platform monitors events such as successes and incidents. The resources of communities can log incidents as they occur, where a log records can include a timestamp and context for each incident. This allows the platform to learn by creating more intelligence to recognize patterns for how and when incidents occur. For example, the platform could determine whether certain events always happen as a function of changes in activities, in certain locations, at certain altitudes, at certain points in time, etc. In some embodiments, the platform can also log incident information related to information obtained from a global positioning system (GPS) tool of a smartphone used by the patient, which can identify a location and other contextual information.

Although many incidents are parts of negative or adverse events, many incidents are also positive and considered successes. Examples include observations that a patient made eye contact, responded to his/her name, held eye contact for a period of time, tried a new food, etc. The platform can collect and utilize both negative and positive events to assess the user and formulate or update a treatment based on the assessment.

In some embodiments, goal tracking can include a process whereby a caregiver logs symptoms that impact their child or patient. The platform can then identifies an appropriate or optimal way to track each symptom, which could be per incident, periodically (e.g., daily, weekly, monthly), or occasionally.

In some embodiments, the platform defines whether a symptom needs to have a field for tracking duration and if the symptom can be measured by its duration or how long each incident lasts. For each symptom, the platform may suggest goals for caregivers to improve the quality of life and health of the patient. In some embodiments, the caregivers can also define their own goals, and define measurement periods or other units.

In some embodiments, the tracked goals are all measurable. The platform can define measurement units and a format for each goal to enable a progress measurement for each goal and for each symptom. In some embodiments, some goals are measured based on the associated success and not just a reduction in intensity or frequency of a symptom. The platform can have predefined associated successes for such goals and measurement units to track success.

In some embodiments, the platform identifies influencers and suggested actions. For example, each symptom can have a set of influencers or triggers. The influencers impact occurrence, intensity, frequency or duration of the symptom. The platform can prepopulate important influencers for each symptom to educate caregivers and initiate control of the influencers.

In some embodiments, the platform can use scientific knowledge that may or may not be readily known, and experience across all caregivers to recommend potential interventions to control each of the triggers that impact a symptom. The platform can identify potential interventions that are measurable actions that can be tracked and measured against progress on specific symptoms.

In some embodiments, the platform can use different intensity scales and/or frequencies. For example, the platform can define a frequency of logging and tracking for each symptom. In some embodiments, not all symptoms need to be measured daily or weekly and not all symptoms change quickly over a short period of time. In some embodiments, each symptom's intensity is measured based on an intensity rating scale ranging from 1-5 as described elsewhere in this disclosure.

The disclosed platform can diagnose various diseases or conditions. For example, the platform can have a list of DSM and comorbidities that are prepopulated as list of conditions across its patient population. In some embodiments, families (e.g., included in a community) or caregivers can log formal diagnosis as documented by a physician or clinician for the patient profiles. The patients may also add diagnosis of diseases that are not populated by the platform. In some instances, the patients may have no official diagnosis but show all the relevant symptoms of some diseases.

In some embodiments, the diagnoses are defined in several categories for the common diseases and their comorbidities. Examples include neurodevelopmental disorders, genetic disorders, neurologic disorders, and/or sensory deficiencies from birth or infancy such as psychiatric disorders, related birth or medical conditions, or other disorders.

The platform may consider various symptom categories. The diagnosis of patients with neurodevelopmental disorders can range across several disease categories. In some embodiments, the platform has pre-defined common conditions that are relevant to a company's (e.g., client of the platform) market strategy. In some embodiments, users can also add and define their own diagnosis to the list.

In some embodiments, the platform defines diagnosis in multiple relevant categories, capturing most of the comorbidities for patients with neurodevelopmental disorders. Examples include general Health, cognitive-developmental health, social-communicative health, emotional health, behavioral health, etc.

Figure 7:
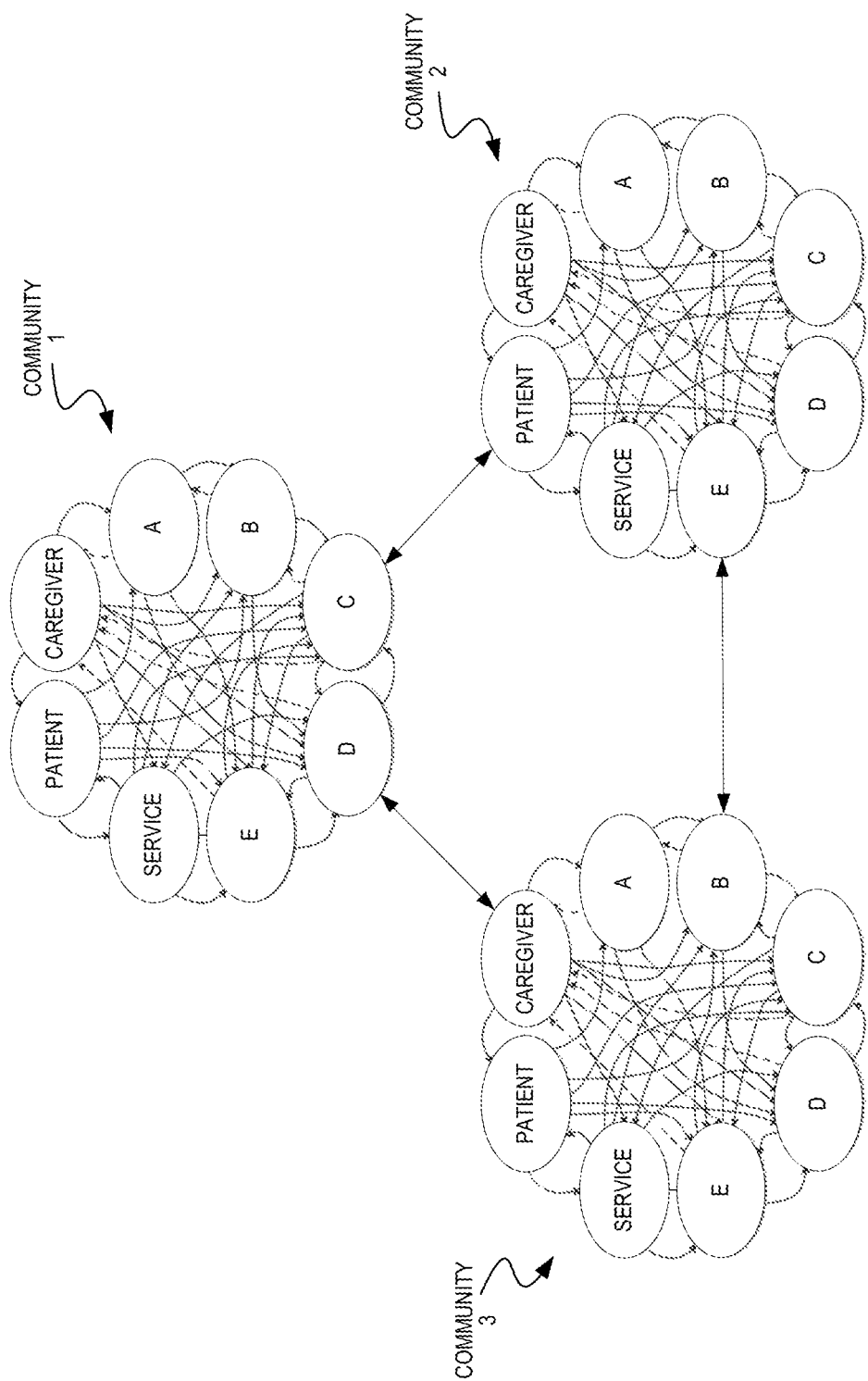
FIG. 7 is a block diagram illustrating interconnected communities of resources for sharing information related to the assessment or treatment of patients according to some embodiments of the present disclosure.

In some embodiments, information collected for patient profiles can be shared across communities. For example, FIG. 7 is a block diagram illustrating interconnected communities of resources according to some embodiments of the present disclosure. The information collected by each community can be uploaded via a service and shared across the entire platform. Anyone providing care for a patient can view or input data about that patient and, with the consent of a caregiver or patient, share that data across the platform. In some embodiments, the sharing is permission-based per data point. Hence, each caregiver of a community can have specific access to some data but not to all data.

The disclosed embodiments can include social platform matching algorithms. For example, families, patients, caregivers, and members of a community can have the option to opt into a social component of the platform including specialized social groups. The platform can match community members to social groups with an artificial intelligence driven matching technique. For example, patients in different communities can be matched based on comorbidities, treatments, genetics, goals, physical regions, environmental factors, and other factors. The communities can be clustered into broader social groups that include multiple patients from different communities. The social groups can share knowledge, ask questions, find mentors, and provide support within their groups. In some embodiments, a physician and other provider can enable the platform to establish social groups that match individuals based on service types, educational background, patient population, research interests, and other defined and customized interests.

The disclosed embodiments can include one or more network portals. For example, the platform may administer a clinical trials portal. A portal for therapeutic or pharmaceutical clinical trials can digitally collect outcomes data in real-time, on a daily basis, or to include adverse events when they occur. In some embodiments, the pharmaceutical portal can have the capacity to view and analyze only data that is relevant to a specific clinical trial and customize the portal for the purposes of that trial, across data types and specific data being collected.

In some embodiments, the network portals can include a consumer facing portal that collects data from patients and associated community members, and provides feedback via, for example, a mobile app. For example, the mobile app can provide feedback and progress data based on input from client devices.

Figure 8A:
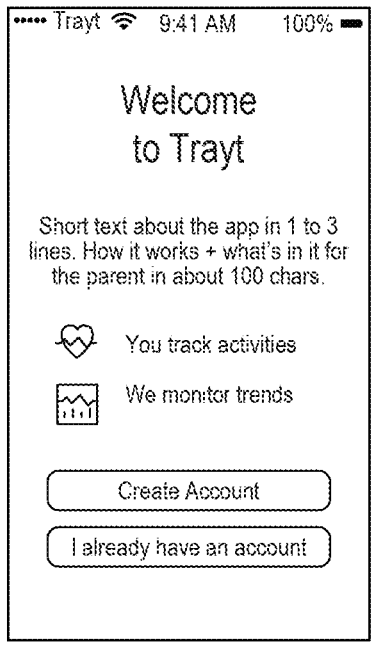
FIGS. 8A through 8Z are screenshots of a mobile application on a client device of the platform according to some embodiments of the present disclosure.
Figure 8B:
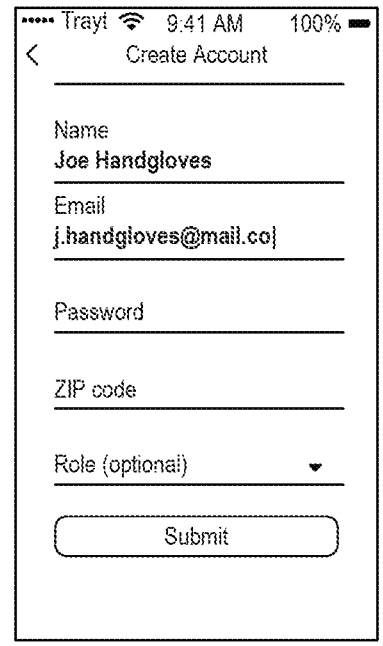
Figure 8C:
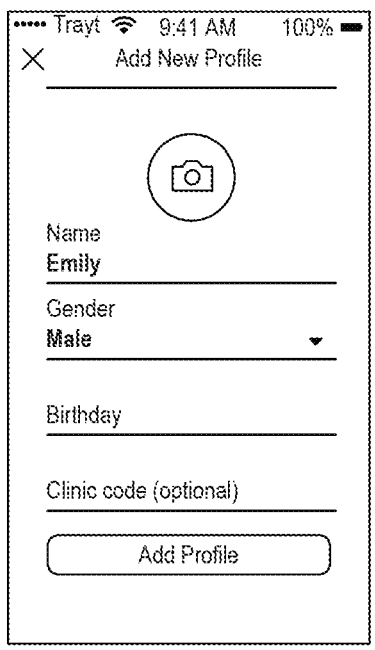
Figure 8D:
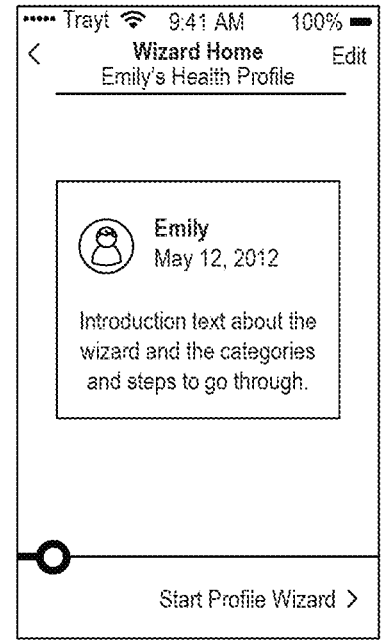
Figure 8E:
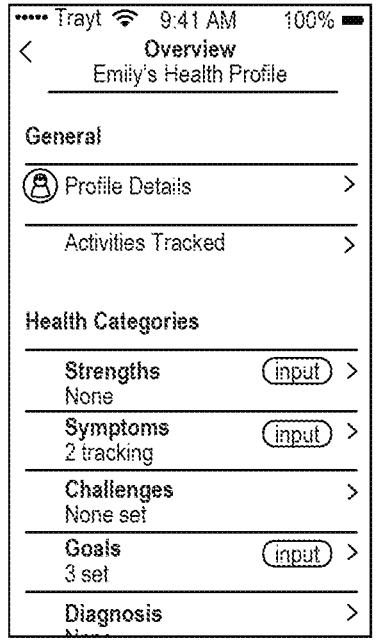
Figure 8F:
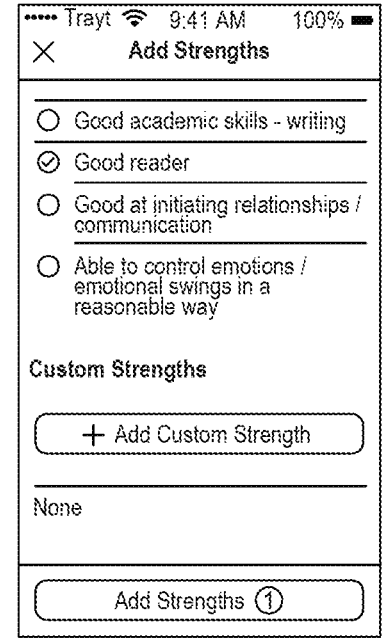
Figure 8G:
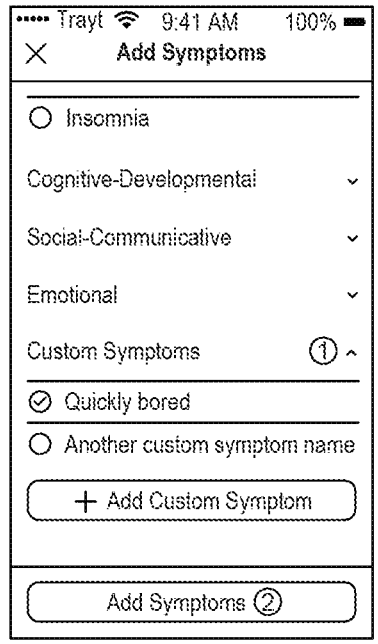
Figure 8H:
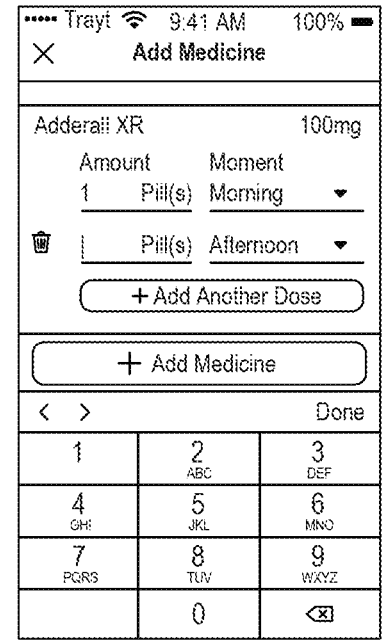
Figure 8I:
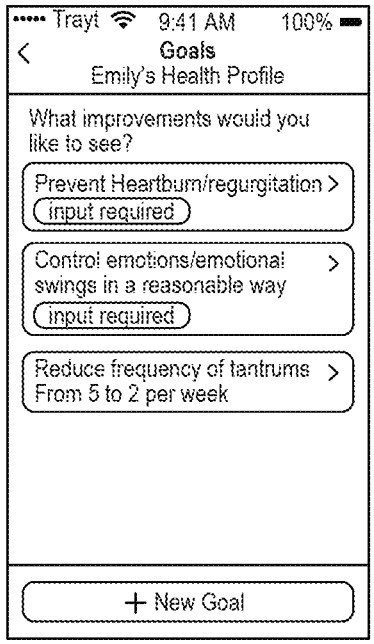
Figure 8J:
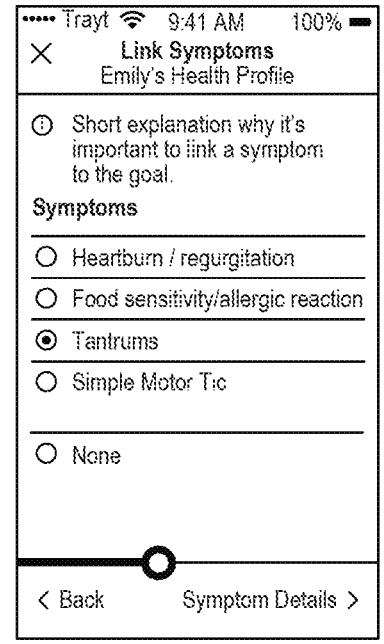
Figure 8K:
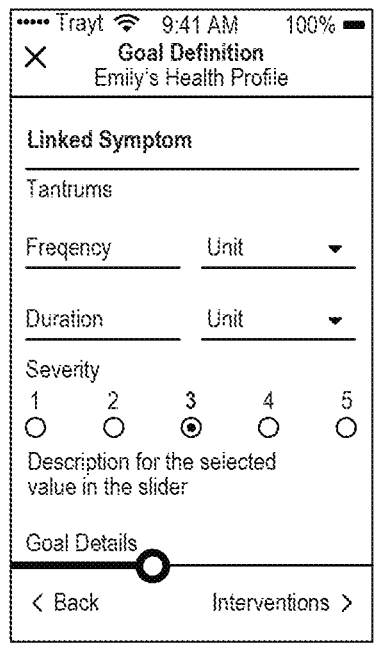
Figure 8L:
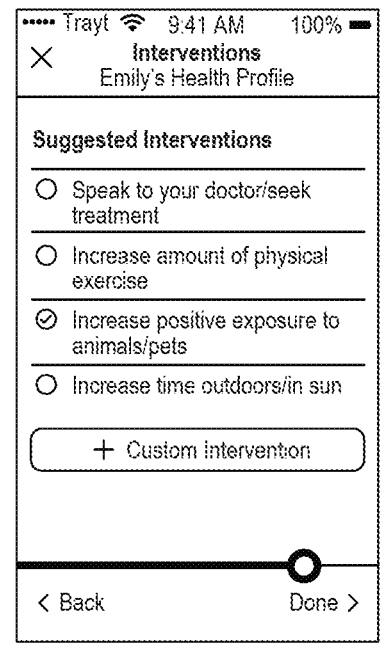
Figure 8Q:
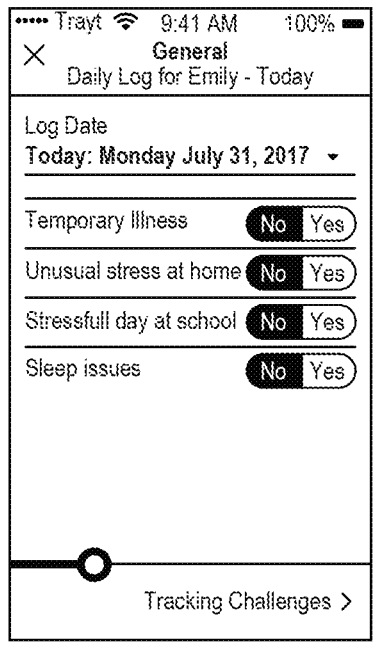
Figure 8R:
Figure 8S:
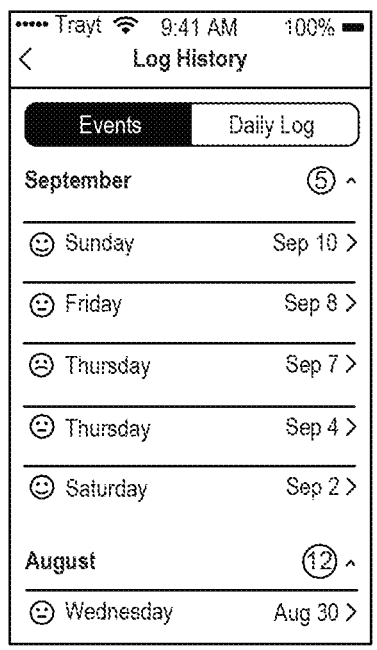
Figure 8T:
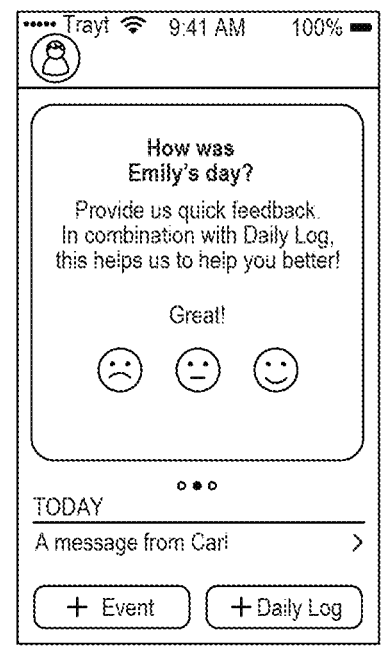
Figure 8U:
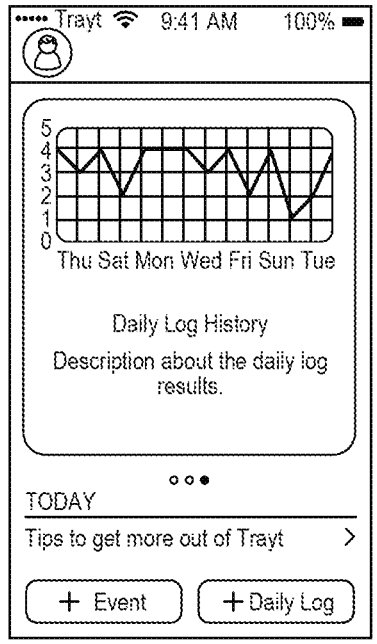
Figure 8V:
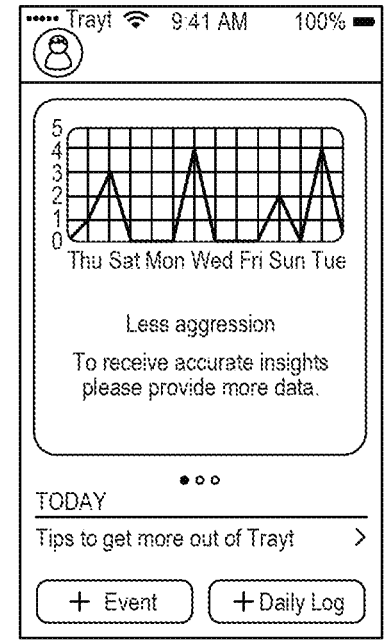
Figure 8W:
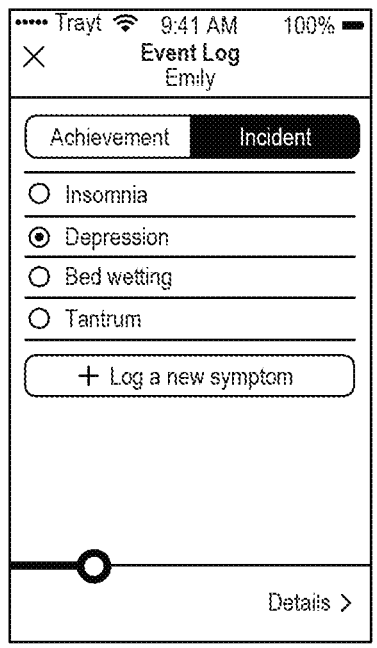
Figure 8X:
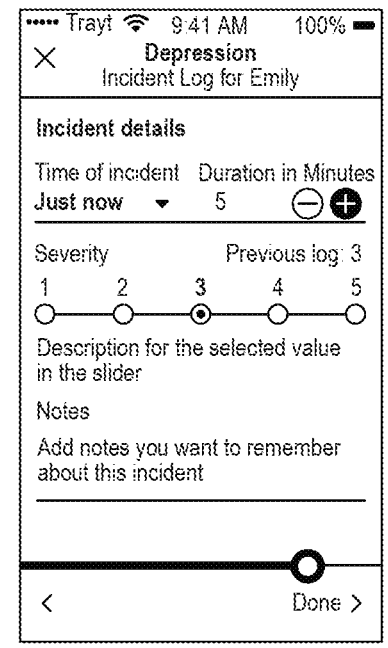
Figure 8Y:
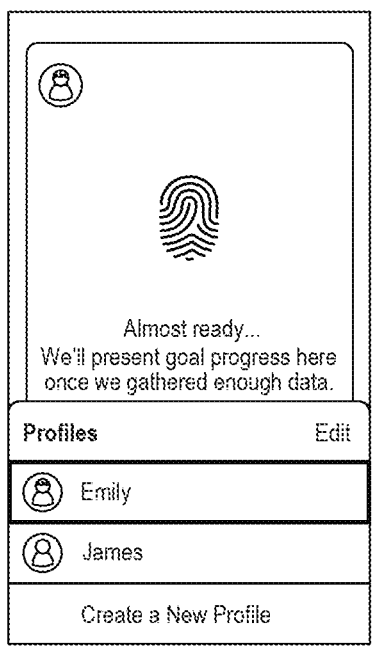
Figure 8Z:
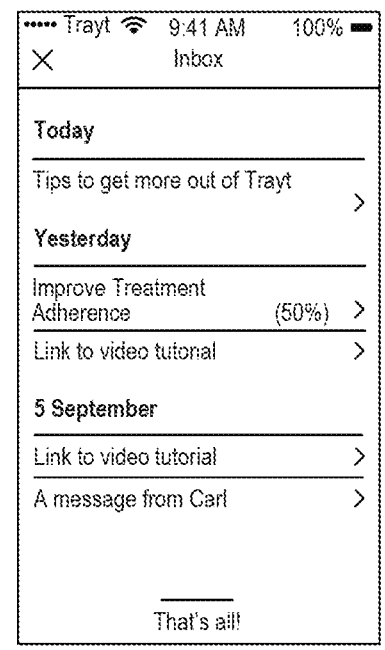

FIGS. 8A through 8Z are screenshots of a mobile app running on the client device 14 of the system 10 according to some embodiments of the present disclosure. In particular, FIGS. 8A through 8Z are screenshots for inputting user-selected and other data items used to build a patient profile including an assessment and a treatment for the patient.

FIG. 8A is an initial welcome screen that includes options to create an account or login to an existing account. When a user selects to create an account, the screenshot of FIG. 8B is displayed to obtain data from the user. Example fields include a name, email, password, zip code, and a role such as caregiver, doctor, sibling, friend, etc. Once the user has registered, the user can login by entering the email and password.

FIG. 8C is a screenshot of an option to add a new profile. In some instances, the profile is for the patient that is being observed by the user. As shown, the user can add a picture, name, gender, birthdate, and clinic code to a profile. FIG. 8D is a screenshot of a profile wizard that can guide a user to input data used to build the user's profile and/or patient's profile.

FIG. 8E is a screenshot of an overview of a health profile. The overview includes a general section and health categories section. The general section includes a profile details section and an activities tracked section. The health categories section includes strengths, symptoms, challenges, goals, diagnosis, etc.

FIG. 8F is a screenshot of options for the strengths including a user-selected "good reader" and has the option to add a customized strength. FIG. 8G is a screenshot of options for symptoms including a user-selected "quickly bored" and has the option to add a customized symptom. FIG. 8H is a screenshot of options for medicines including adding a medicine, amount, and time to taking the medicine.

FIG. 8I is a screenshot of goals that can be set for the patient. The goals include preventing heartburn/regurgitation, control emotions/emotional swings in a reasonable way, and reduce frequency of tantrums. FIG. 8J is a screenshot for linking one or more symptoms to a goal. FIG. 8K is a screenshot of items that can be selected to define the linked symptom. FIG. 8L is a screenshot for selecting interventions.

FIG. 8M is a screenshot of tracked challenges. As shown, the challenge is a migraine defined by selecting according to selectable items. FIG. 8N is a screenshot of a treatment adherence including binary selectable Yes/No answers. FIG. 8O is a screenshot of a summary for a certain day. FIG. 8P is a screenshot of a list of selected activities that are being tracked.

FIG. 8Q is a screenshot of a general log of monitored data. As shown, the user can select from multiple binary Yes/No options. FIG. 8R is a screenshot of a log history including events and enables for selecting a daily log. FIG. 8S shows the daily log that includes graphical indicators for each day. FIG. 8T is a screenshot of an interface for a user to indicate the status of a day be selecting one of three options.

FIG. 8U is a screenshot that includes a graphical visualization of a daily log history. FIG. 8V is a screenshot that includes a graphical visualization of the patient's aggression on a daily basis. FIG. 8W is a screenshot for setting an event log for particular symptoms. FIG. 8X is a screenshot for setting features of a depression incident. FIG. 8Y is a screenshot for a user to select between different profiles. Lastly, FIG. 8Z is a screenshot of an inbox portal that can be used for retrieving emails.

Figure 9:
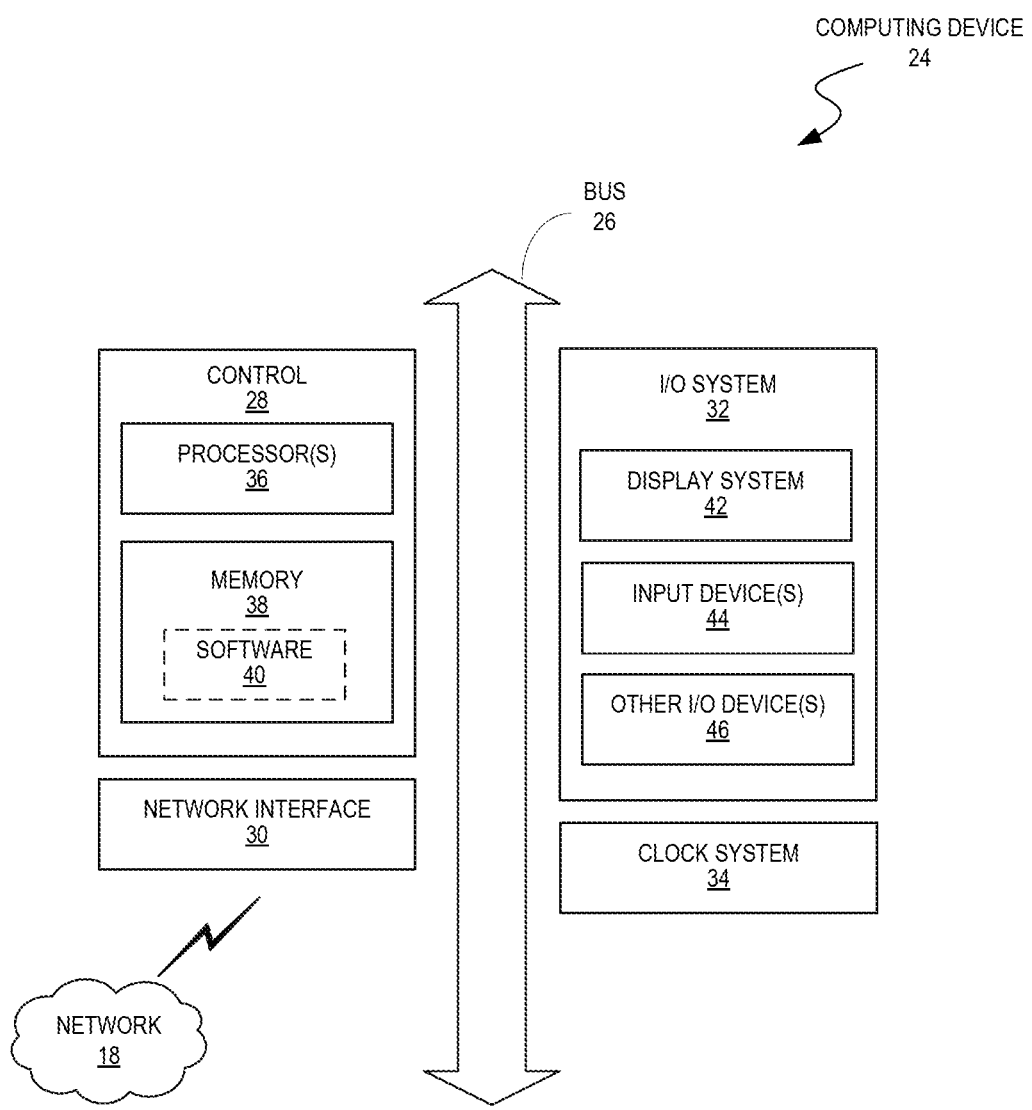
FIG. 9 is a block diagram illustrating a computing device operable to implement aspects of the disclosed technology according to some embodiments of the present disclosure.

FIG. 9 is a block diagram illustrating a computing device operable to implement aspects of the disclosed technology according to some embodiments of the present disclosure. The computing device 24 may be a generic computer or specifically designed to carry out features of system 10. For example, the computing device 24 may be a system-on-chip (SOC), a single-board computer (SBC) system, a desktop or laptop computer, a kiosk, a mainframe, a mesh of computer systems, a handheld mobile device, or combinations thereof.

The computing device 24 may be a standalone device or part of a distributed system that spans multiple networks, locations, machines, or combinations thereof. In some embodiments, the computing device 24 operates as a server computer (e.g., the comorbidity server 12 or healthcare information sources 16), as a client device (e.g., the client devices 14) in a client-server network environment, or as a peer machine in a peer-to-peer system. In some embodiments, the computing device 24 may perform one or more steps of the disclosed embodiments in real time, near real time, offline, by batch processing, or combinations thereof As illustrated in FIG. 9, the computing device 24 includes a bus 26 that is operable to transfer data between hardware components. These components include a control 28 (e.g., processing system), a network interface 30, an input/output (I/O) system 32, and a clock system 34. The computing device 24 may include other components that are not shown nor further discussed for the sake of brevity. One having ordinary skill in the art will understand any hardware and software that is included but not shown in FIG. 9.

The control 28 includes one or more processors 36 (e.g., central processing units (CPUs)), application-specific integrated circuits (ASICs), and/or field-programmable gate arrays (FPGAs), and memory 38 (which may include software 40). For example, the memory 38 may include volatile memory, such as random-access memory (RAM) and/or non-volatile memory, such as read-only memory (ROM). The memory 38 can be local, remote, or distributed.

A software program (e.g., software 40), when referred to as "implemented in a computer-readable storage medium," includes computer-readable instructions stored in the memory (e.g., memory 38). A processor (e.g., processor 36) is "configured to execute a software program" when at least one value associated with the software program is stored in a register that is readable by the processor. In some embodiments, routines executed to implement the disclosed embodiments may be implemented as part of operating system (OS) software (e.g., Microsoft Windows® and Linux®) or a specific software application, component, program, object, module, or sequence of instructions referred to as "computer programs."

As such, the computer programs typically include one or more instructions set at various times in various memory devices of a computer (e.g., computing device 24), which, when read and executed by at least one processor (e.g., processor 36), will cause the computer to perform operations to execute features involving the various aspects of the disclosed embodiments. In some embodiments, a carrier containing the aforementioned computer program product is provided. The carrier is one of an electronic signal, an optical signal, a radio signal, or a non-transitory computer-readable storage medium (e.g., memory 38).

The network interface 30 may include a modem or other interfaces (not shown) for coupling the computing device 24 to other computers over the network 18. The I/O system 32 may operate to control various I/O devices including peripheral devices, such as a display system 42 (e.g., a monitor or touch-sensitive display) and one or more input devices 44 (e.g., a keyboard and/or pointing device). Other I/O devices 46 may include, for example, a disk drive, printer, scanner, or the like. Lastly, the clock system 34 controls a timer for use by the disclosed embodiments.

Operation of a memory device (e.g., memory 38), such as a change in state from a binary one (1) to a binary zero (0) (or vice versa) may include a visually perceptible physical change or transformation. The transformation may include a physical transformation of an article to a different state or thing. For example, a change in state may involve accumulation and storage of charge or a release of stored charge. Likewise, a change of state may include a physical change or transformation in magnetic orientation or a physical change or transformation in molecular structure, such as a change from crystalline to amorphous or vice versa.

Aspects of the disclosed embodiments may be described in terms of algorithms and symbolic representations of operations on data bits stored in memory. These algorithmic descriptions and symbolic representations generally include a sequence of operations leading to a desired result. The operations require physical manipulations of physical quantities. Usually, though not necessarily, these quantities take the form of electronic or magnetic signals that are capable of being stored, transferred, combined, compared, and otherwise manipulated. Customarily, and for convenience, these signals are referred to as bits, values, elements, symbols, characters, terms, numbers, or the like. These and similar terms are associated with physical quantities and are merely convenient labels applied to these quantities.

While embodiments have been described in the context of fully functioning computers, those skilled in the art will appreciate that the various embodiments are capable of being distributed as a program product in a variety of forms and that the disclosure applies equally, regardless of the particular type of machine or computer-readable media used to actually effect the embodiments.

While the disclosure has been described in terms of several embodiments, those skilled in the art will recognize that the disclosure is not limited to the embodiments described herein and can be practiced with modifications and alterations within the spirit and scope of the invention. Those skilled in the art will also recognize improvements to the embodiments of the present disclosure. All such improvements are considered within the scope of the concepts disclosed herein. Thus, the description is to be regarded as illustrative instead of limiting.

The invention claimed is:

1. A method comprising:
receiving, by a computer system, data communicated over one or more networks from disparate sources;
configuring, by the computer system, a first patient profile based on the received data to track effectiveness of a treatment for an unclassified disease or unclassified condition, wherein the first patient profile is configured based on:
(i) user-specified values selected for the first patient on a first instance of a patient assessment software application running on a client device, the user-specified values being selected from a range indicating severity for a first symptom or first diagnosis of an unclassified disease or condition,
(ii) genomic data of the first patient including a target DNA sequence having a marker for a classified disease or condition and a non-target DNA sequence, and
(iii) sensor data periodically generated and indicative of a risk factor value of the first patient;
processing, by the computer system, a plurality of patient profiles including the first patient profile using an Apriori algorithm,
wherein processing the plurality of patient profiles using the Apriori algorithm comprises:
identifying, by the computer system, patterns in the plurality of patient profiles that relate non-target DNA sequences to symptom data or diagnosis data including a genetic mutation that relates to the first symptom or the first diagnosis of the first patient, and
generating, by the computer system, a plurality of comorbidity profiles based on the identified patterns,
wherein the identified patterns define the plurality of comorbidity profiles and a comorbidity profile is indicative of a presence of an unclassified comorbid symptom or unclassified diagnosis common to a first condition and a second condition; and
performing, by the computer system, an assessment based on data obtained from a second instance of the patient assessment tool used to build a second patient profile associated with a second patient, such that an outcome of the assessment matches a second symptom or diagnosis to an unclassified comorbid symptom or diagnosis of one of the plurality of comorbidity profiles so as to associate the second patient profile with the matching comorbidity profile,
wherein performing the assessment comprises:
determining causal relationships between dimensions of the plurality of patient profiles and the second patient profile based on a Bayesian network that discovers relationships between unclassified combinations of symptoms or conditions and treatments; and
deriving, using a data mining algorithm, a vector of scores for each comorbidity profile such that a highest score for the matching comorbidity profile identifies a treatment for the second patient; and
training the Bayesian network based on an outcome of the data mining algorithm including the vector of scores for each comorbidity profile to improve classification and reclassification of patient profiles as being associated with specific comorbidity profiles.

2. The method of claim 1, wherein the received data comprises a plurality of responses to a plurality of questions of an electronic survey, the plurality of questions having been presented via the patient assessment tool on the client device.

3. The method of claim 2, wherein the received data is indicative of a severity value of the first symptom, the severity value being based on at least one of an intensity integer value, a frequency value, or a duration value of the first symptom adjusted by the computer system based on at least one of an age value or a gender value for the first patient.

4. The method of claim 2, wherein the received data is indicative of a severity value of the first symptom, the severity value being based on an intensity integer value, a frequency value, and a duration value that are each adjusted by the computer system based on an age value and a gender value for the first patient.

5. The method of claim 1, wherein building the first patient profile based on the received data comprises:
building the first patient profile based on a plurality of severity values for a plurality of symptoms including the first symptom.

6. The method of claim 1, wherein the first condition is a health-related abnormality corresponding to a neurodevelopmental disorder diagnosable based on a first assessment and the second condition is a medical condition that is diagnosable based on a second assessment that is distinct from the first assessment.

7. The method of claim 1, further comprising, prior to performing the assessment:
receiving contextual information indicative of an occurrence of an event related to the first patient's activity, wherein the contextual information indicates any of a change in the first patient's activity, a location of the first patient when the event occurred, an environmental condition at the first patient's location when the event occurred, or a point in time when the event occurred; and updating the first patient profile with the contextual information to influence the outcome of the assessment that matches the second symptom to the comorbid symptom of one of the plurality of comorbidity profiles.

8. The method of claim 1, wherein the outcome of the assessment includes information about a treatment for the comorbid symptom, the method further comprising:

causing an electronic message to be sent to the client device, the electronic message including guidance for implementing the treatment.

9. The method of claim 1, wherein the first symptom is of a disorder classified in the Diagnostic and Statistical Manual of Mental Disorders (DSM).

10. The method of claim 1 further comprising:
selecting a measurable goal for treating the first patient; and
causing an electronic message to be sent to the client device, the electronic message including the selected measurable goal as a suggestion for treating the first patient based on the assessment matching.

11. The method of claim 1, wherein the first patient is a child and a user of the client device is a parent of the child.

12. The method of claim 1, further comprising:
obtaining, by the computer system, a dataset about a plurality of symptoms experienced by the first patient, each symptom being associated with a condition and characterized by a plurality of values for an intensity, a frequency, and a duration of the symptom;
wherein said assessment comprises discovering, by the computer system, based on the dataset, a coexistence of simultaneous conditions that are independent of each other but contribute to at least some of the plurality of symptoms;
the method further comprising:
ascertaining, by the computer system, a treatment for the simultaneous conditions based on a result of the discovering; and
selecting, by the computer system, an action for treating the simultaneous conditions to achieve an objective, the objective including a change in symptoms experienced by the patient.

13. The method of claim 12, wherein the coexistence of simultaneous conditions is a comorbidity of the patient.

14. The method of claim 12, wherein the objective is a selected goal, the method further comprising:
tracking a progress of the selected goal and electronically communicating suggestions to a client device for additional actions, the additional actions depending on a level of the progress, wherein the additional actions are identified based on symptoms impacted by the selected goal;
sending an electronic message to the client device, the electronic message including guidance for implementing the additional actions; and
automatically updating the first patient profile with the selected goal and the tracked progress.

15. The method of claim 14, wherein each of the selected goal and the additional action is measurable by at least two of intensity, frequency, or duration.

16. A computer system comprising:
a processor; and
a memory storing instructions, execution of which by the processor causes the computer system to perform operations comprising:
receiving data from a first instance of a patient assessment tool on a client device, the received data indicating a first symptom experienced by a first patient or a first diagnosis of the first patient;
configuring a first patient profile based on the received data to track effectiveness of a treatment for an unclassified disease or unclassified condition, wherein the first patient profile is configured based on:
  (i) user-specified values selected for the first patient on a first instance of a patient assessment software application running on a client device, the user-specified values being selected from a range indicating severity for a first symptom or first diagnosis of an unclassified disease or condition,
  (ii) genomic data of the first patient including a target DNA sequence having a marker for a classified disease or condition and a non-target DNA sequence, and
  (iii) sensor data periodically generated and indicative of a risk factor value of the first patient;
analyzing a plurality of patient profiles including the first patient profile using an Apriori algorithm, the Apriori algorithm configured to identify patterns in the plurality of patient profiles that relate genetic data to symptom data or diagnosis data;
generating a plurality of comorbidity profiles based on the identified patterns, wherein each comorbidity profile is indicative of a presence of a comorbid symptom or diagnosis common to a first condition and a second condition; and
performing an assessment based on data obtained from a second instance of the patient assessment tool used to build a second patient profile associated with a second patient, such that an outcome of the assessment matches a second symptom or diagnosis to an unclassified comorbid symptom or diagnosis of one of the plurality of comorbidity profiles so as to associate the second patient with the matching comorbidity profile
wherein performing the assessment comprises:
  determining causal relationships between dimensions of the plurality of patient profiles and the second patient profile based on a Bayesian network that discovers relationships between unclassified combinations of symptoms or conditions and treatments;
  deriving, using a data mining algorithm, a vector of scores for each comorbidity profile such that a highest score for the matching comorbidity profile identifies a treatment for the second patient; and
  training the Bayesian network based on an outcome of the data mining algorithm including the vector of scores for each comorbidity profile to improve classification and reclassification of patient profiles as being associated with specific comorbidity profiles.

17. The computer system of claim 16, wherein the received data comprises a plurality of responses to a plurality of questions of an electronic survey, the plurality of questions having been presented via the patient assessment tool on the client device, and wherein the received data is indicative of a severity value of the first symptom, the severity value being based on at least one of an intensity integer value, a frequency value, or a duration value of the first symptom adjusted by the computer system based on at least one of an age value or a gender value for the first patient.

18. The computer system of claim 16, wherein building the first patient profile based on the received data comprises:
building the first patient profile based on a plurality of severity values for a plurality of symptoms including the first symptom.

19. The computer system of claim 16, wherein the first condition is a health-related abnormality corresponding to a neurodevelopmental disorder diagnosable based on a first assessment and the second condition is a medical condition that is diagnosable based on a second assessment that is distinct from the first assessment.

20. The computer system of claim 16, wherein the outcome of the assessment includes information about a treatment for the comorbid symptom, and wherein execution of the instructions further causes the computer system to perform operations comprising:
causing an electronic message to be sent to the client device, the electronic message including guidance for implementing the treatment.

21. The computer system of claim 16, said operations further comprising:
obtaining a dataset about a plurality of symptoms experienced by the first patient, each symptom being associated with a condition and characterized by a plurality of values for an intensity, a frequency, and a duration of the symptom;
wherein said assessment comprises discovering, based on the dataset, a coexistence of simultaneous conditions that are independent of each other but contribute to at least some of the plurality of symptoms;
said operations further comprising:
ascertaining a treatment for the simultaneous conditions based on a result of the discovering; and
selecting an action for treating the simultaneous conditions to achieve an objective, the objective including a change in symptoms experienced by the patient.

22. The computer system of claim 21, wherein the coexistence of simultaneous conditions is a comorbidity of the patient.

23. The computer system of claim 21, wherein the objective is a selected goal, said operations further comprising:
tracking a progress of the selected goal and electronically communicating suggestions to a client device for additional actions, the additional actions depending on a level of the progress, wherein the additional actions are identified based on symptoms impacted by the selected goal;
sending an electronic message to the client device, the electronic message including guidance for implementing the additional actions; and
automatically updating the first patient profile with the selected goal and the tracked progress.

24. The computer system of claim 23, wherein each of the selected goal and the additional action is measurable by at least two of intensity, frequency, or duration.

25. A non-transitory machine-readable storage medium tangibly embodying instructions, execution of which by a computer system causes the computer system to perform operations comprising:
receiving data from a first instance of a patient assessment tool on a client device, the received data indicating a first symptom experienced by a first patient or a first diagnosis of the first patient;
building a first patient profile based on the received data;
analyzing a plurality of patient profiles including the first patient profile using an Apriori algorithm, the Apriori algorithm configured to identify patterns in the plurality of patient profiles that relate genetic data to symptom data or diagnosis data;
generating a plurality of comorbidity profiles based on the identified patterns, wherein each comorbidity profile is indicative of a presence of a comorbid symptom or diagnosis common to a first condition and a second condition; and
performing an assessment based on data obtained from a second instance of the patient assessment tool used to build a second patient profile associated with a second patient, such that an outcome of the assessment matches a second symptom or diagnosis to a comorbid symptom or diagnosis of one of the plurality of comorbidity profiles so as to associate the second patient with the matching comorbidity profile,
wherein performing the assessment comprises:
determining causal relationships between dimensions of the plurality of patient profiles and the second patient profile based on a Bayesian network that discovers relationships between unclassified combinations of symptoms or conditions and treatments;
deriving, using a data mining algorithm, a vector of scores for each comorbidity profile such that a highest score for the matching comorbidity profile identifies a treatment for the second patient; and
training the Bayesian network based on an outcome of the data mining algorithm including the vector of scores for each comorbidity profile to improve classification and reclassification of patient profiles as being associated with specific comorbidity profiles.

26. The method of claim 1, wherein an output of the Apriori algorithm includes dimensions in an N-dimensional feature space, and wherein generating the plurality of comorbidity profiles further comprises:
embedding the plurality of patient profiles as points in the N-dimensional feature space;
applying a clustering algorithm to the embedded points to generate clusters of the plurality of patient profiles; and
generating a comorbidity profile in the plurality of comorbidity profiles based on at least one of the clusters.

27. The method of claim 1, further comprising:
using a Bayesian network to determine a causal relationship between a treatment and at least one symptom in the matching comorbidity profile.

* * * * *